(12) United States Patent
Hayashi et al.

(10) Patent No.: US 7,149,341 B2
(45) Date of Patent: Dec. 12, 2006

(54) WAFER INSPECTION APPARATUS

(75) Inventors: Yoshinori Hayashi, Kanagawa (JP); Hiroyuki Naraidate, Iwate (JP); Hiroaki Yuda, Iwate (JP); Atsushi Tanabe, Shibata (JP); Hiromichi Isogai, Shibata (JP); Koji Izunome, Shibata (JP)

(73) Assignees: Toshiba Ceramics Co., Ltd., Tokyo (JP); Shibaura Mechatronics Corporation, Yokohama (JP)

( * ) Notice: Subject to any disclaimer, the term of this patent is extended or adjusted under 35 U.S.C. 154(b) by 866 days.

(21) Appl. No.: 10/361,857

(22) Filed: Feb. 11, 2003

(65) Prior Publication Data

US 2003/0169916 A1 Sep. 11, 2003

(30) Foreign Application Priority Data

Feb. 19, 2002 (JP) ............................. 2002-042398

(51) Int. Cl.
*G06K 9/00* (2006.01)
*G01N 21/00* (2006.01)

(52) U.S. Cl. .................................... 382/145; 356/237.4
(58) Field of Classification Search ........ 382/145–152; 356/237.4
See application file for complete search history.

(56) References Cited

U.S. PATENT DOCUMENTS

| 5,461,417 | A | * | 10/1995 | White et al. ................. 348/131 |
| 5,592,295 | A | * | 1/1997 | Stanton et al. ............... 356/426 |
| 5,768,443 | A | * | 6/1998 | Michael et al. ............. 382/294 |
| 5,822,055 | A | * | 10/1998 | Tsai et al. ................. 356/237.1 |
| 6,147,357 | A | * | 11/2000 | Nicolesco ............... 250/559.46 |
| 6,432,800 | B1 | * | 8/2002 | Park ........................... 438/582 |
| 6,449,585 | B1 | * | 9/2002 | Hyun et al. .................. 702/183 |
| 6,798,503 | B1 | * | 9/2004 | Hiramoto et al. ........ 356/237.1 |

(Continued)

FOREIGN PATENT DOCUMENTS

JP 8-136462 A 5/1996

(Continued)

OTHER PUBLICATIONS

The Wafer's Edge, Alexander E. Braun, Senior Editor—Semiconductor International, Mar. 1, 2006, http://www.reed-electronics.com/semiconductor/article/CA6309190.html.*

*Primary Examiner*—Joseph Mancuso
*Assistant Examiner*—Hadi Akhavannik
(74) *Attorney, Agent, or Firm*—Foley & Lardner LLP

(57) ABSTRACT

A wafer inspection apparatus has a supporting means (10) for rotatably supporting a wafer (W) formed of a disk, a circumferential edge imaging means (40) for imaging a circumferential edge (S) of the wafer (W) that is supported by the supporting means for rotation, a notch imaging means (50) for imaging a notch (N), a notch illumination part (52) for illuminating the notch (N), and a control means (70) for processing image data imaged by the circumferential edge imaging means (40) and the notch imaging means (50). The circumferential edge imaging means (40) has a plurality of imaging cameras (41) for imaging a plurality of different parts in a thickness direction of the circumferential edge of the wafer (W). The different parts of the circumferential edge (S) of the wafer (W) include an apex at right angles to a surface of the wafer (W) and a front side bevel and a back side bevel inclined relative to the apex. The notch imaging means (50) for the wafer (W) having the notch (N) has a plurality of imaging cameras (51) for imaging different parts in the thickness direction of the notch (N).

15 Claims, 25 Drawing Sheets

U.S. PATENT DOCUMENTS

| | | |
|---|---|---|
| 6,906,794 B1 * | 6/2005 | Tsuji ........................ 356/237.4 |
| 6,923,045 B1 * | 8/2005 | Neo et al. ...................... 73/105 |
| 6,947,588 B1 * | 9/2005 | Sim ........................... 382/149 |
| 7,013,222 B1 * | 3/2006 | Strader ........................ 702/30 |
| 7,079,237 B1 * | 7/2006 | Woo et al. ................ 356/237.2 |
| 2003/0202178 A1 * | 10/2003 | Tsuji et al. ............... 356/237.2 |
| 2005/0023491 A1 * | 2/2005 | Young et al. .......... 250/559.42 |
| 2005/0036671 A1 * | 2/2005 | Watkins et al. ............. 382/145 |
| 2005/0237529 A1 * | 10/2005 | Kanno et al. ............... 356/426 |

FOREIGN PATENT DOCUMENTS

| | | |
|---|---|---|
| JP | 10-038539 A | 2/1998 |
| JP | 2000-114329 A | 4/2000 |
| JP | 3197329 B2 | 6/2001 |
| JP | 3200308 B2 | 6/2001 |
| JP | 2001-221749 A | 8/2001 |

* cited by examiner

FIG.25

| | rank | line defect | point defect | plane defect |
|---|---|---|---|---|
| upper face | 1 | | | |
| | 2 | | | |
| | 3 | | | |
| | : | | | |
| | 10 | | | |
| side face | 1 | | | |
| | 2 | | | |
| | 3 | | | |
| | : | | | |
| | 10 | | | |
| lower face | 1 | | | |
| | 2 | | | |
| | 3 | | | |
| | : | | | |
| | 10 | | | |
| notch | 1 | | | |
| | 2 | | | |
| | 3 | | | |
| | : | | | |
| | 10 | | | |

FIG.26

| rank 1 | angle (deg) | line defect | point defect | plane defect |
|---|---|---|---|---|
| upper face | 0 | | | |
| | 10 | | | |
| | 20 | | | |
| | : | | | |
| | 350 | | | |
| side face | 0 | | | |
| | 10 | | | |
| | 20 | | | |
| | : | | | |
| | 350 | | | |
| lower face | 0 | | | |
| | 10 | | | |
| | 20 | | | |
| | : | | | |
| | 350 | | | |
| notch | bottom | | | |
| | left | | | |
| | right | | | |
| | upper | | | |
| | lower | | | |

| rank 2 | angle (deg) | line defect | point defect | plane defect |
|---|---|---|---|---|
| | 0 | | | |
| | : | | | |

WAFER INSPECTION APPARATUS

TECHNICAL FIELD

The present invention relates to a wafer inspection apparatus for imaging a circumferential edge of a wafer formed of a disk and inspecting the wafer based on image data without destruction.

RELATED ART

A prior wafer inspection apparatus is described, for example, in Japanese Patent Unexamined Publication No.8-136462.

This wafer inspection apparatus includes, as shown in FIG. 34, a support 1, an imaging camera 2, and a monitor (not shown). The support 1 rotatably supports a wafer W formed of a disk. The imaging camera 2 continuously images a circumferential edge S of the wafer W that is supported by the support 1 and rotated. The monitor, such as CRT, displays an image obtained by the imaging camera 2.

The imaging camera 2 is provided movably all around the wafer W and rotatably in a thickness direction of the wafer W. By this movement and rotation, an operation direction and a distance of the imaging camera are adjusted.

The circumferential edge S of the wafer W is displayed on the monitor to observe defect or not on the circumferential edge S of the wafer W by rotating the wafer W and by moving and rotating the imaging camera 2 all around or in the thickness direction.

In the foregoing wafer inspection apparatus, although the image where an imaging direction of the imaging camera 2 is at right angles thereto is clear, the image where the imaging direction of the imaging camera 2 is inclined easily becomes unclear. Therefore, accuracy of detecting defects is bad.

As shown in FIG. 34, the circumferential edge S of the wafer W has an apex SS, a front side bevel SA, and a back side bevel SB. The apex SS is at right angles to the wafer face. The front side bevel SA and the back side bevel SB are inclined relative to the apex SS and beveled. If the imaging direction is adjusted to the apex at right angles by moving and rotating the imaging camera 2 in a thickness direction, for example, the front side bevel SA and the back side bevel SB are imaged with an inclined manner relative to the imaging direction of the imaging camera 2. Therefore, the image becomes unclear. As a result, accuracy of imaging becomes bad.

Further, there was a problem such that the apex SS, the front side bevel SA, and the back side bevel SB could not be observed simultaneously in a clear condition.

SUMMARY OF THE INVENTION

An object of the present invention is to provide a wafer inspection apparatus, which can improve accuracy of imaging and improve accuracy of detection of defects, by clearly imaging a plurality of different parts in a thickness direction, even if a circumferential edge of a wafer is beveled so as to be inclined relative to an apex.

According to one embodiment of the invention, a wafer inspection apparatus has a supporting means, a circumferential edge imaging means, and a control means. The supporting means rotatably supports a wafer formed of a disk. The circumferential edge imaging means continuously images a circumferential edge of the wafer that is supported by the supporting means and rotated. The control means processes imaging data imaged by the circumferential edge imaging means.

The circumferential edge imaging means has a plurality of imaging cameras for imaging a plurality of different parts of the circumferential edge of the wafer in the thickness direction.

When inspecting the wafer, the wafer is supported by the supporting means and rotated. In this state, an image of the circumferential edge is obtained by the circumferential edge imaging means. In this case, if the circumferential edge imaging means is provided with the plurality of imaging cameras for imaging the plurality of different parts in the thickness direction of the circumferential edge of the wafer, whole parts in the thickness direction can be imaged clearly and simultaneously, without moving positions of the imaging cameras, even if the circumferential edge of the wafer is beveled to be inclined. Operation of imaging the edge faces is improved. Accuracy of imaging is improved.

The image data obtained are sent to the control means and processed by a graphical processor.

Preferably, the plurality of image cameras are constituted of line sensors that image substantially linearly along the thickness direction of the circumferential edge of the wafer. When the circumferential edge is imaged with a narrow width and continued, resolution of edge images becomes good. Accuracy of imaging is improved.

The plurality of parts of the circumferential edge includes, for example, three faces, namely an apex, a front side bevel, and a back side bevel. The apex is substantially at right angles to the surface of the wafer. The front side bevel and the back side bevel (e.g. inclined faces by beveling) are inclined relative to the apex. An apex imaging camera, a front side bevel imaging camera, and a back side bevel imaging camera are positioned in such a condition that imaging directions thereof are at right angles to the apex, the front side bevel, and the back side bevel, respectively. When these three cameras are provided, three faces of the circumferential edge can be imaged clearly and simultaneously. Operation of imaging the edge faces is improved. Accuracy of imaging is improved.

Preferably, each imaging camera is positioned so that it can image positions of the circumferential edge of the wafer with the same phase position. In this case, because the imaging cameras can be put together, the whole apparatus is compacted.

Preferably, a circumferential edge illumination part is provided for illuminating the circumferential edge. The circumferential edge illumination part has an aggregate of optical fibers. The optical fibers illuminate the illumination light so as to form an illuminated plane along a certain arc in a thickness direction of the circumferential edge of the wafer and to converge the illumination light toward the center of the arc. Each imaging camera is positioned in a bright field of a reflection light.

Each imaging camera is positioned so as to receive the illumination light from a C-shape circumferential edge illumination part in regular reflection. Three faces of the circumferential edge can be imaged clearly and simultaneously. Particularly, defects can be imaged well. Accuracy of imaging is improved accordingly.

Further, preferably, the control means is provided with an image data processing means and a display such as CRT. The image data processing means has a circumferential edge displaying means for simultaneously displaying the circumferential edge of the wafer that is imaged by the plurality of imaging cameras of the circumferential edge imaging means on the display in such a condition that each phase of the angle positions is matched.

Thus, conditions of three faces of the circumferential edge, particularly defects can be observed. In this case, because the plurality of imaging cameras image the plurality of different parts (faces) of the circumferential edge of the wafer, three faces can be observed clearly and simultaneously, even if the circumferential edge of the wafer is beveled and inclined. Accuracy of inspection is improved accordingly.

Preferably, the image data processing means has a defect recognizing means and a defect coordinate displaying means. The defect recognizing means recognizes the area as the defect, the area having a difference of brightness relative to a standard brightness to be based from the image data of the circumferential edge of the wafer and the image data. The defect coordinate displaying means displays a coordinate of the defect identified by the defect recognizing means on the display. In this case, because the position of the defect can be determined, accuracy of inspection is improved accordingly.

Preferably, the defect coordinate displaying means has an angle coordinate displaying function and a thickness direction displaying function. The angle coordinate display function is to display an angle coordinate along the peripheral direction regarding the circumferential edge of the wafer. The thickness direction coordinate display function is to display a relative position along the thickness direction of the circumferential edge of the wafer. In this case, displaying is reliable.

Further, preferably, the image data processing means has a defect form recognizing means and a defect form displaying means. The image data processing means recognizes the form of the defect identified by the defect recognizing means. The defect form displaying means displays the form identified by the defect form recognizing means on the display. In this case, because the form of the defect can be categorized, accuracy of inspection is improved accordingly.

The defect form recognizing means has a function of classifying into one of point defects, line defects, and plane defect and recognizing, based on a predetermined threshold value. In this case, because the defects are classified into some kinds, recognizing becomes easy.

Preferably, a defect distribution calculating means is provided for calculating distribution of point defects, line defects, and plane defects at certain unit of angles on the image face of each imaging camera of the circumference of the wafer. In this case, because the distribution of the defects on the circumferential edge is recognized, it can be utilized for solution of defect generation. Accuracy of inspection is improved accordingly.

Preferably, a defect ranking means is provided for sizing at a certain angle unit of point defects, line defects, and plane defects at each imaging face of the imaging camera. In this case, because the size degree of defects on the circumferential edge is recognized, it can be utilized for solution of defect generation. Accuracy of inspection is improved accordingly.

Preferably, the image data processing means has a defect area calculating means, a defect area displaying means, a defect circumscribed rectangle size calculating means, and a defect circumscribed rectangle size displaying means. The defect area calculating means obtains an area of the defect identified by the defect recognizing means. The defect area displaying means displays the area calculated by the defect area calculating means. The defect circumscribed rectangle size calculating means obtains the size of a rectangle circumscribing the defect that is identified by the defect recognizing means. The defect circumscribed rectangle size displaying means displays the size calculated by the defect circumscribed rectangle size calculating means on the display. In this case, the size of the defect can be categorized. Accuracy of inspection is improved accordingly.

Preferably, the image data processing means has a defect density calculating means and a defect density displaying means. The defect density calculating means obtains a density of the defect from the area of the defect calculated by the defect area calculating means and from the size of the circumscribed rectangle calculated by the defect circumscribed rectangle size calculating means. The defect density displaying means displays the density of the defect calculated by the defect density calculating means. In this case, an extent of the defect can be recognized. Accuracy of inspection is improved accordingly.

Preferably, the image data processing means has a defect brightness calculating means and a defect brightness displaying means. The defect brightness calculating means obtains a mean brightness of the defect identified by the defect recognizing means. The defect brightness displaying means displays the mean brightness calculated by the defect brightness calculating means on the display. In this case, because of the brightness of the defect corresponds to a depth of the defect, the depth of the defect can be recognized. Accuracy of inspection is improved accordingly.

The image data processing means has a quality judging means and a wafer quality displaying means. The quality judging means judges qualities of the wafer based on the defect identified by the defect recognizing means. The wafer quality displaying means displays the qualities of the wafer judged by the quality judging means on the display. Because the qualities of the wafer can be judged automatically, inspection becomes easy.

When the circumferential edge of the wafer has a notch (e.g. a notch that has a bottom and two side parts, and that is cutout in a substantially U-shape), a notch imaging means is provided for imaging the notch. When the notch has an apex, a front side bevel and a back side bevel, five cameras are provided. Here the apex is substantially at right angles to a surface of the wafer. The front side bevel and the back side bevel are beveled and inclined relative to the apex. The five cameras are a bottom apex imaging camera, a bottom front side bevel imaging camera, a bottom back side bevel imaging camera, one side part-apex imaging camera, and the other side part-apex imaging camera. The bottom apex imaging camera corresponds to the apex of the bottom of the notch. The bottom front side bevel imaging camera corresponds to the front side bevel of the bottom of the notch. The bottom back side bevel imaging camera corresponds to the back side bevel of the bottom. The one side part-apex imaging camera corresponds to the apex of one side part. The other side part-apex imaging camera corresponds to the other apex of the other side part of the notch. Three faces of the notch can be imaged clearly and simultaneously. Operation of imaging the edge faces is improved. Accuracy of imaging is improved.

Preferably, a notch illumination part for illuminating the notch and a control means are provided as well as the other parts but the notch of the circumferential edge of the wafer.

Preferably, the supporting means for the wafer is provided rotatably around the central axis for the rotating center, and has a supporting board and a driving part. The supporting board has a plurality of support fingers. The plurality of support fingers are provided on a circumference around the central axis for supporting the circumferential edge of the wafer and provided. The driving part rotates the supporting board. When the wafer is supported by the support fingers, bad influence such as damaging the surface of the wafer is avoided. Each support finger is provided with a supporting face for supporting the circumferential edge of the wafer, which is inclined downward to the central axis. Because the circumferential edge is supported by the support face of the circumferential edge of the wafer, bad influence such as damaging the face of the wafer is further avoided.

Further, preferably, the supporting means is provided with a support position changing system for changing the support position of the wafer that is supported by the support fingers of the supporting board. In this case, because the support position is changed, the parts that cannot be imaged by the support fingers can be exposed and imaged.

The support position changing system has, preferably, a plurality of carrying fingers. The plurality of carrying fingers are provided rotatably around the central axis of the supporting board as a center for carrying the circumferential edge of the wafer and provided on the circumference around the central axis. The support position changing means has a carrying board and a moving system. The carrying board is constituted to move to two positions (a carrying position where the carrying fingers are carried and lifted to a higher position than the support fingers of the supporting board and a delivery position where the wafer is delivered to the support fingers at a lower position than the support fingers). The moving system moves the carrying board to two positions, namely the carrying position and the delivery position.

Thus, when the support position of the wafer is changed, the carrying board at the delivery position is moved to the carrying position. The wafer supported by the supporting board is carried and lifted by the carrying fingers of the carrying board. During lifting, the supporting board is rotated. The support fingers of the supporting board are positioned to the other angle phase position. Then, the carrying board is positioned at the delivery position. The wafer is delivered to the supporting fingers. In this case, because the supporting position is changed, parts that could not be imaged formerly can be exposed and imaged. Further, because the wafer is carried and lifted by the carrying fingers of the carrying board, bad influence such as damaging the wafer is avoided.

Preferably, a wafer transfer is provided for transferring the wafer to be inspected from a storage of the wafer and supporting the wafer in centering to the support fingers of the supporting board of the supporting means. Thus, because the wafer is centered and supported relative to the support fingers of the supporting board, accuracy of positioning the wafer relative to the supporting board becomes high. Accuracy of inspection thereafter is improved.

Preferably, the wafer transfer has a pair of carrying hands. The pair of carrying hands is provided with an engaging means for engaging the circumferential edge of the wafer. The carrying hands are movable relatively in the holding position and the release position. At a holding position, the carrying hands hold the wafer by the engaging means in a face direction of the wafer. At a release position, holding is released. At the carrying position, the engaging means is provided with an elastic contact body for elastically contacting the wafer. The carrying hands engage the engaging means with the circumferential edge of the wafer at the carrying position and carries the wafer in the face direction of the wafer. Because of this carrying, an elastic contact body of the engaging means is elastically contacted. The wafer becomes centripetal. The wafer is easily centered relative to the supporting fingers of the supporting board of the supporting means.

Preferably, the diameter measuring means measures the diameter of the wafer supported by supporting means and rotated. Inspection of the diameter of the wafer and inspection of the defect is done simultaneously.

BRIEF DESCRIPTION OF THE DRAWINGS

Embodiments of a wafer inspection apparatuses according to the present invention are explained by reference to the following drawings.

FIG. 10($b$) is a front view thereof.

FIG. 13($b$) is a front view thereof.

FIG. 14($b$) is a front view thereof.

FIG. 25 shows a method for a defect ranking means of a wafer inspection apparatus according to the present invention.

FIG. 26 shows a method for a defect distribution calculating means of a wafer inspection apparatus according to the present invention.

EMBODIMENTS

In a wafer inspection apparatus shown in FIGS. 1~11, a wafer W to be inspected is formed of a disk.

Figure 12:
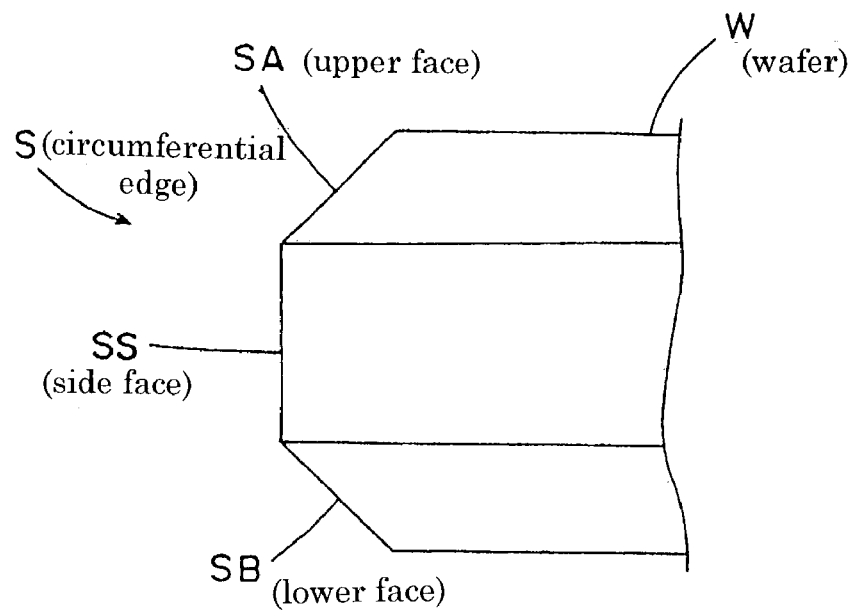
FIG. 12 shows a structure of a circumferential edge of a wafer to be inspected by a wafer inspection apparatus according to the present invention.
Figure 13:
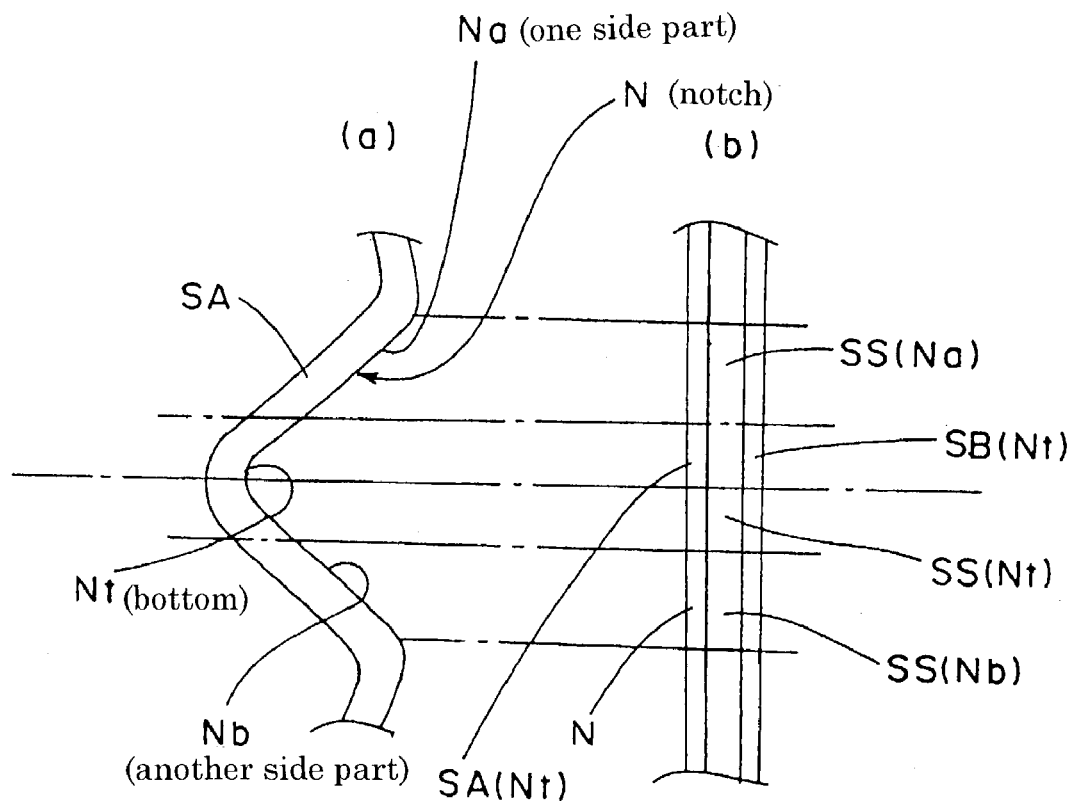
FIG. 13($a$) is a plane view showing a structure of a notch of a wafer to be inspected by a wafer inspection apparatus according to the present invention.
Figure 14:
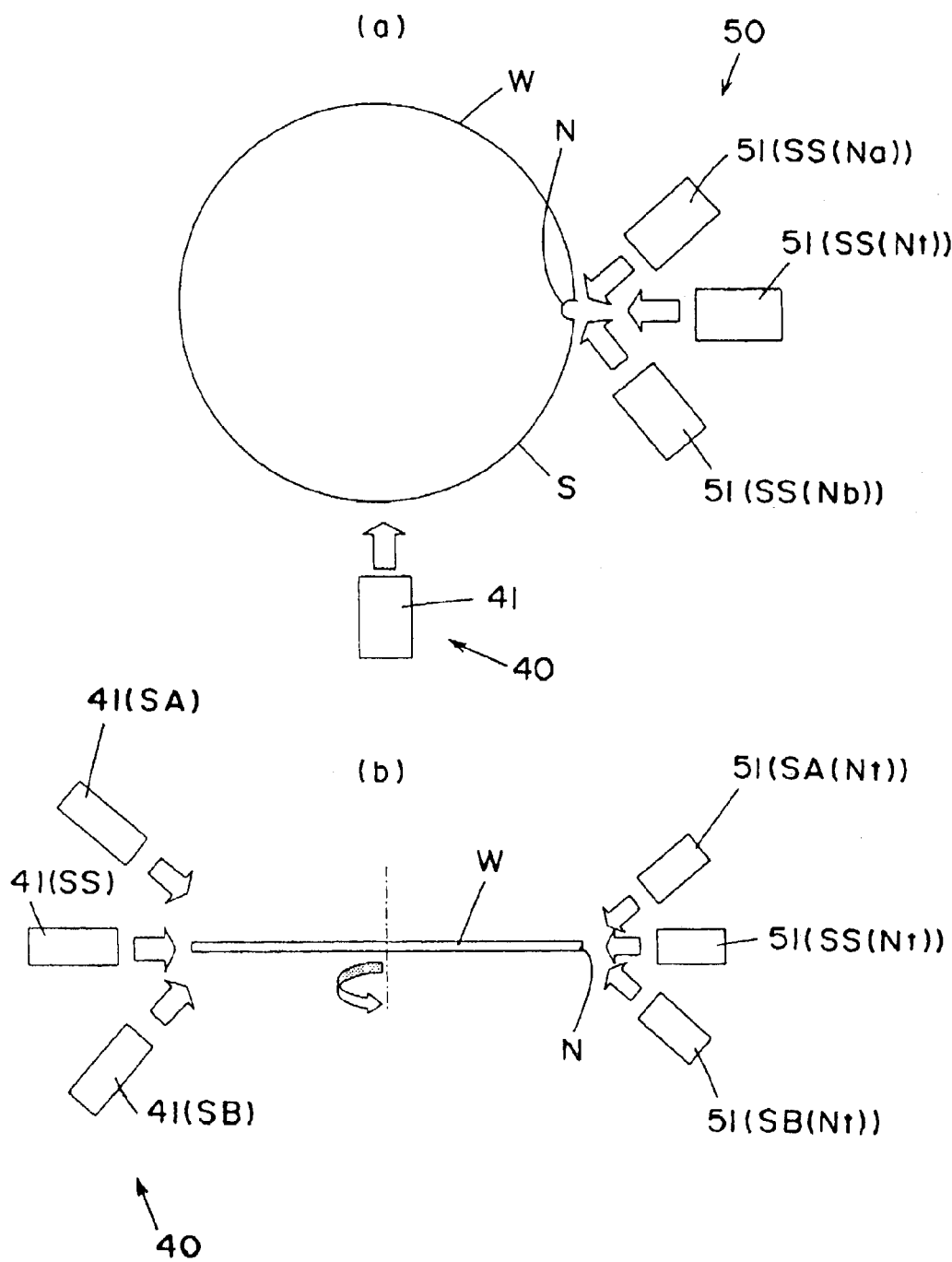
FIG. 14($a$) is a plane view showing a relationship of positions of imaging cameras relative to a wafer of a wafer inspection apparatus according to the present invention.
Figure 15:
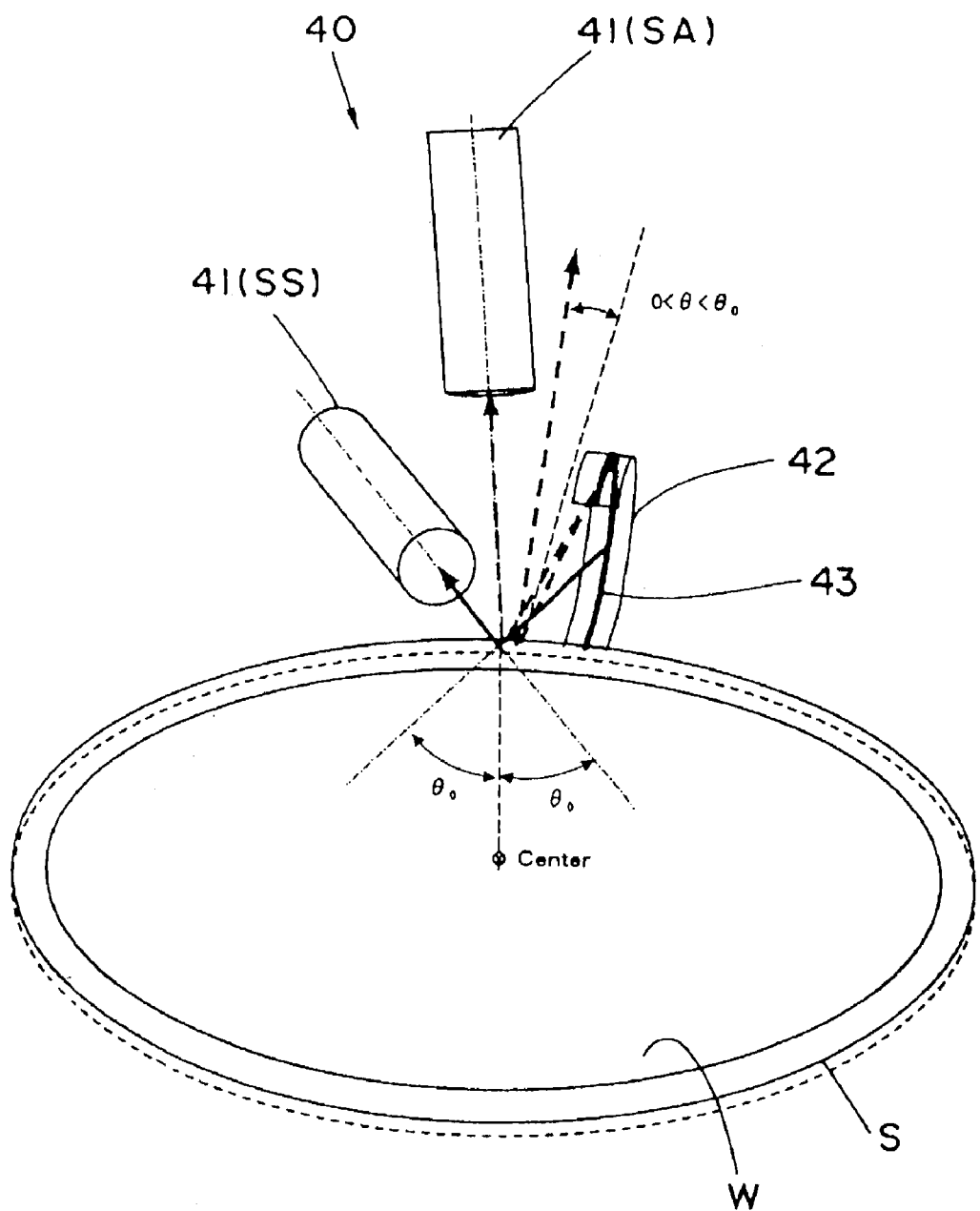
FIG. 15 is a perspective view showing a relationship between an imaging means for a circumferential edge and an illuminating means for a circumferential edge of a wafer inspection apparatus according to the present invention.

Particularly, as shown in FIGS. 12 and 13, a circumferential edge S of the wafer W has an apex SS, a front side bevel SA, and a back side bevel SB. The apex SS is substantially at right angles to a surface of the wafer W. The front side bevel SA and the back side bevel SB are inclined relative to the apex SS. Upper and lower parts of the circumferential edge S are beveled so as to incline the front side bevel SA and the back side bevel SB.

Further, at a predetermined position in a peripheral direction of the circumferential edge S of the wafer W, a notch (namely a notch N that includes a bottom Nt, one side part Na and the other side part Nb and that is cutout in a substantially U-shape) is formed.

On the notch N, the apex SS, the front side bevel SA, and the back side bevel SB are also formed. The apex SS is substantially at right angles to a surface of the wafer W. The front side bevel SA and the back side bevel SB are beveled and inclined relative to the apex SS. The diameter of the wafer W is, for example, set to 300 mm.

The wafer inspection apparatus of this embodiment has a supporting means 10, a circumferential edge imaging means 40, a notch imaging means 50, and a control means 70. The supporting means 10 rotatably supports the wafer W formed of a disk. The circumferential edge imaging means 40 continuously images the circumferential edge S of the wafer W that is supported by the supporting means 10 and rotated. The notch imaging means 50 images the notch N. The control means 70 processes imaging data imaged by the circumferential edge imaging means 40 and imaging data imaged by the notch imaging means 50.

Because the notch imaging means 50 has substantially the same constitution as the circumferential edge imaging means 40, description of the notch imaging means 50 is omitted.

Figure 7:
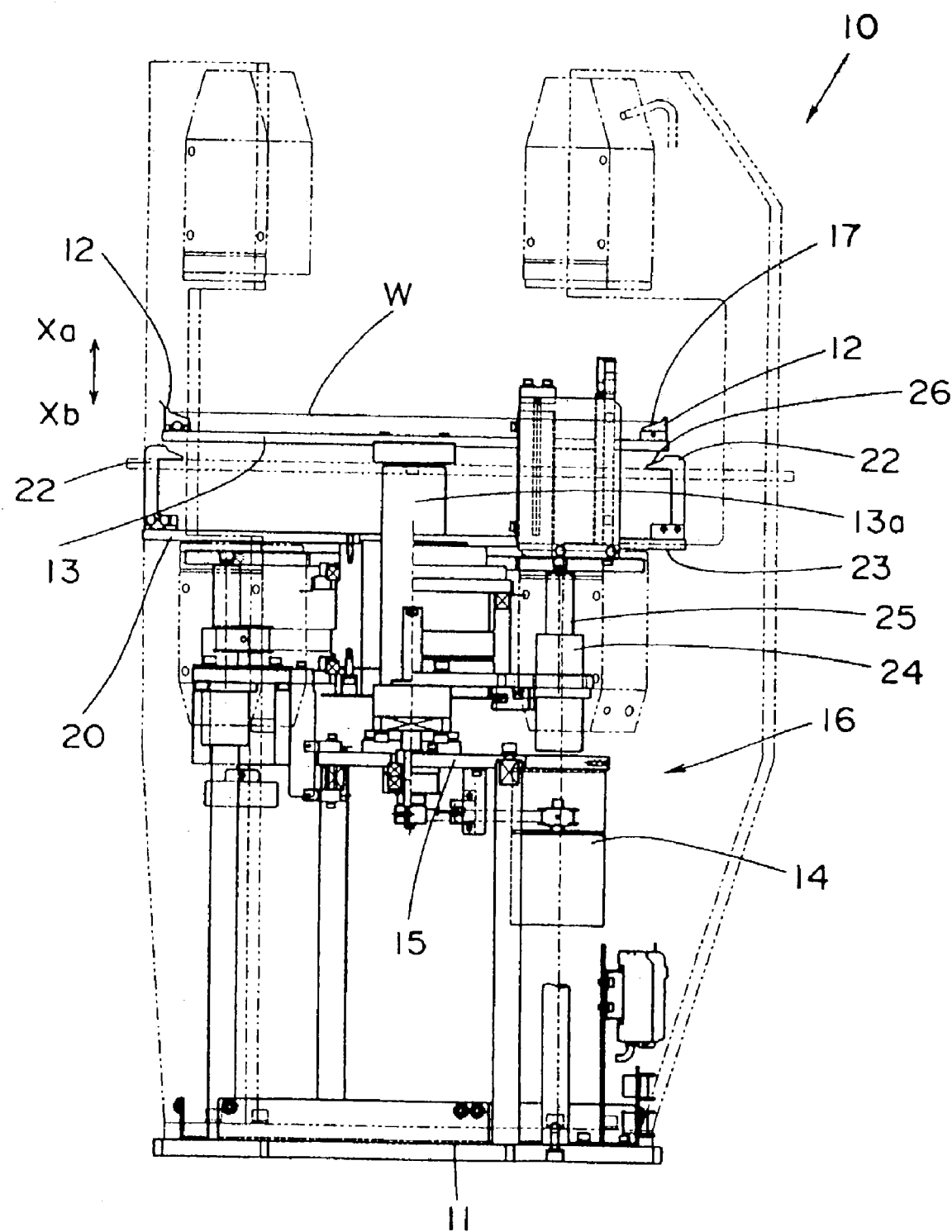
FIG. 7 is a front view showing a supporting means of a wafer inspection apparatus according to the present invention.
Figure 8:
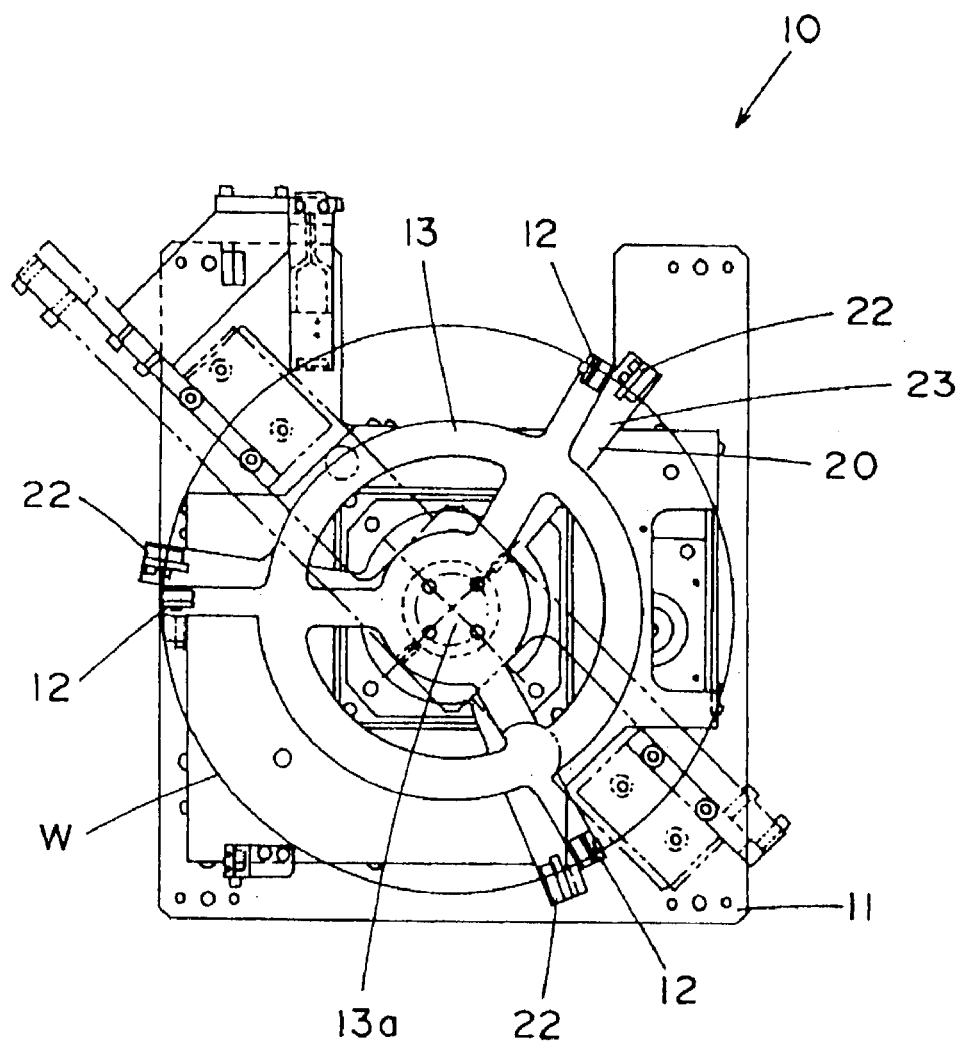
FIG. 8 is a plane view showing a supporting means of a wafer inspection apparatus according to the present invention.
Figure 9:
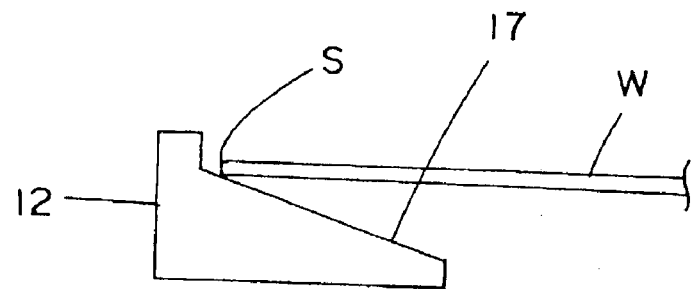
FIG. 9 is an enlarged view showing a support finger at a supporting means of a wafer inspection apparatus according to the present invention.

The supporting means 10 has, as shown in FIG. 1 to FIG. 9 and FIG. 33 (mainly as shown in FIG. 7 to FIG. 9), a base 11, a supporting board 13, and a driving part 16. The supporting board 13 has a plurality of support fingers 12. The plurality of support fingers 12 are provided on the base 11 rotatably around a central axis 13a as a rotating center for supporting the circumferential edge S of the wafer W and provided on a circumference around the central axis 13a. The driving part 16 comprises a motor 14 and a belt transmission system 15 for rotating the supporting board 13.

The support fingers 12 of the supporting board 13 are provided at three equiangular positions. As shown in FIG. 9, a supporting face 17 is formed for supporting the circumferential edge S of the wafer W that is inclined downward to the central axis 13a.

Further, the supporting means 10 is provided with a support position changing means 20 for changing a support position of the wafer W supported by the support fingers 12 of the supporting board 13.

The support position changing means 20 is provided with, as shown in FIG. 1 to FIG. 9 and FIG. 33 (as mainly shown in FIG. 7 to FIG. 9), a plurality (three in the embodiment) of carrying fingers 22. The plurality of carrying fingers 22 are provided rotatably around the central axis 13a of the supporting board 13 as a center for carrying the circumferential edge S of the wafer W and provided on the circumference around the central axis 13a. Further, the support position changing means 20 has a carrying board 23 and a slider type moving system 25. The carrying board 23 is constituted so as to move the carrying fingers 22 to a carrying position Xa ((b) (c) in FIG. 33) and a delivery position Xb ((a) (d) in FIG. 33). The carrying position Xa is an upper position than the support fingers 12 of the supporting board 13 where the wafer W is carried and lifted. The delivery position Xb is a lower position than the support fingers 12 where the wafer W is delivered to the support fingers 12. The slider type moving system 25 has a motor driving system 24 and moves the carrying board 23 to the carrying position Xa and the delivery position Xb. When positioning in the carrying position Xa (position (b) in FIG. 3), the support fingers 12 are set to another angle phase position by rotating the supporting board 13 (position (c) in FIG. 3). In this position, it is supported again by the support fingers 12 of the supporting board 13 (position (d) in FIG. 3). Each carrying finger 22 is also provided with a support face 26 that is inclined downward to the central axis 13*a* for supporting the circumferential edge S of the wafer W.

Further, in the shown embodiment, a wafer transfer 30 transfers the wafer W to be inspected from a storage 31 of the wafer and supports the wafer W in centering to the support fingers 12 of the supporting board 13 of the supporting means 10. In detail, the wafer transfer 30 is provided with a pair of two engaging means 32 and a pair of carrying hands 33, 33. The engaging means 32 engage the circumferential edge of the wafer W. The carrying hands 33, 33 hold the wafer W by the engaging means 32 in a face direction of the wafer W at a holding position Ya. At a release position Yb, holding is released. The carrying hands 33, 33 are movable relatively in the holding position Ya and the release position Yb.

Figure 11:
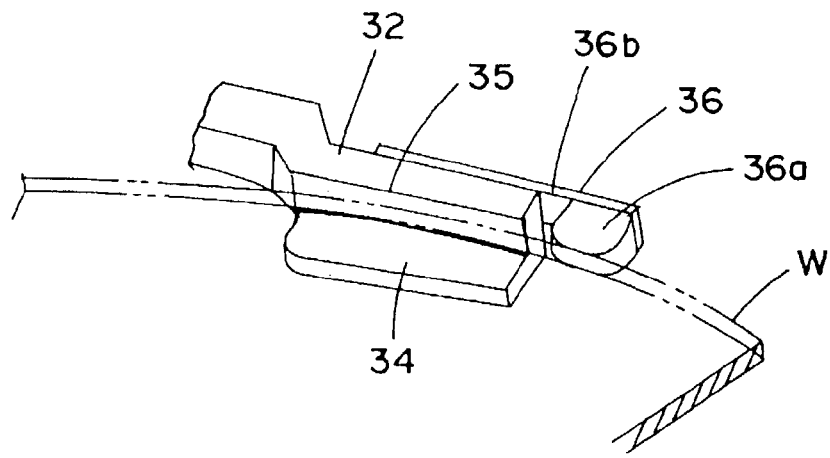
FIG. 11 is an enlarged perspective view showing an engaging means of a wafer transfer of a wafer inspection apparatus according to the present invention.

Each engaging means 32 is provided with, as shown in FIG. 11, a support face 34, a limit face 35, and an elastic contact 36. The support face 34 supports the circumferential edge of the wafer W. The limit face 35 limits the circumferential edge S of the wafer W for moving outside. The elastic contact 36 elastically contacts the circumferential edge S of the wafer W at the holding position.

The elastic contact 36 comprises an abutting member 36*a* and a plate spring 36*b*. The abutting member 36*a* abuts the circumferential edge S of the wafer W. The plate spring 36*b* has one end provided with the abutting member 36*a* and the other end fixed to the limit face 35 for elastically abutting the abutting member 36*a* with the wafer W.

The circumferential edge imaging means 40 is provided with an imaging camera for an apex 41 (SS), an imaging camera for a front side bevel 41 (SA), and an imaging camera for a back side bevel 41 (SB). These cameras are positioned so that the imaging directions are at right angles to the faces. Each imaging camera 41 is provided on an arranging bed 44 so that the imaging means can image positions of the circumferential edge S of the wafer W with the same phase. Because the imaging cameras 41 are put together, the whole apparatus can be compacted.

Further, in the embodiment shown in FIG. 1 to FIG. 6, FIG. 15 and FIG. 16, a circumferential edge illumination part 42 is provided for illuminating the edge S of the wafer W. The circumferential edge illumination part 42 has an aggregate of optical fibers 43 and is formed in a C-shape. The optical fibers 43 illuminate the illumination light to form an illuminated plane along a certain arc in a thickness direction of the circumferential edge S of the wafer W and to converge the illumination light toward the center of the arc. Each imaging camera 41 is provided on the arranging bed 44 so that the illumination light from the circumferential edge illumination part 42 positions in a bright field of a reflected light. Each imaging camera 41 is constituted of a line sensor, and is provided so that it receives the illumination light from the C-shape circumferential edge illumination part 42 in regular reflection.

In detail, for example, the front side bevel imaging camera 41 (SA) and the back side bevel imaging camera 41 (SB) are provided at 25° relative to the vertical direction in consideration with the upper and back side bevels of the wafer W having angles of 20°~30° relative to the horizontal direction.

Figure 16:
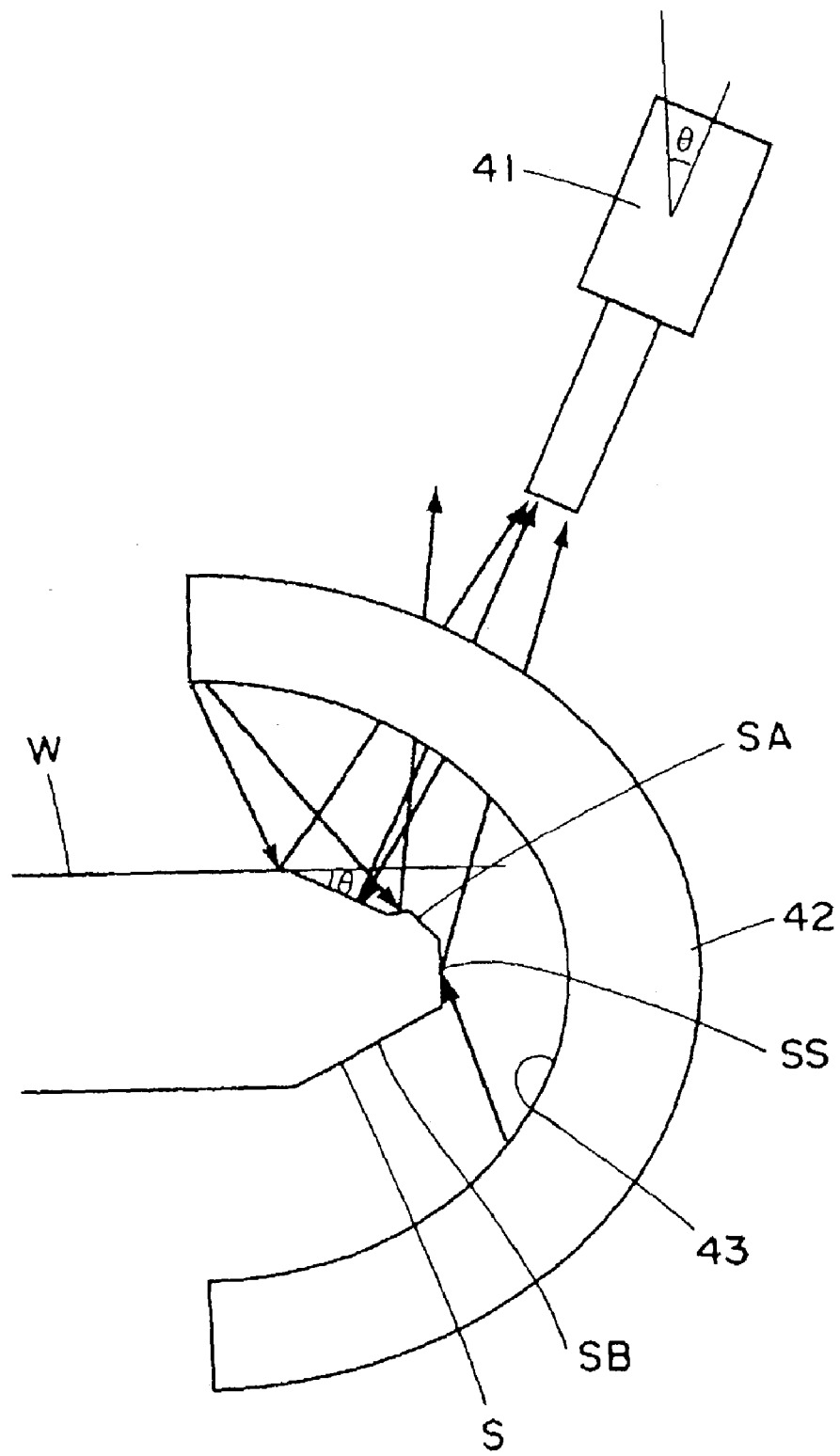
FIG. 16 is a side view showing a relationship between an imaging means for a circumferential edge and an illuminating means for a circumferential edge of a wafer inspection apparatus according to the present invention.

Because imaging is done in such an optical system, as shown in FIG. 16, a part where the regular reflected light is not incident, such as a pit or projection becomes dark. It is detected as a defect by image processing described later.

The notch imaging means 50 has, as shown in FIG. 1 to FIG. 5, FIG. 6, FIG. 14, a plurality (five) of imaging cameras 51 for imaging a plurality (five) of different parts in a thickness direction of the notch N. Each camera 51 is constituted of an area sensor for imaging as an area.

In detail, the notch imaging means 50 has the five imaging cameras 51. These correspond to the apex SS, the front side bevel SA, and the back side bevel SB, and are positioned so that each imaging direction will be at right angles to the face. The notch imaging means 51 has a bottom apex imaging camera 51 (SS(Nt)), a bottom front side bevel imaging camera 51 (SA(Nt)), a bottom back side bevel imaging camera 51 (SB(Nt)), one side part-apex imaging camera 51 (SS(Na)), and the other side part-apex imaging camera 51 (SS(Nb)). The bottom apex imaging camera 51 (SS(Nt)) corresponds to the apex SS of the bottom Nt of the notch N. The bottom front side bevel imaging camera 51 (SA(Nt)) corresponds to the front side bevel SA of the bottom Nt of the notch N. The bottom back side bevel imaging camera 51 (SB(Nt)) corresponds to the back side bevel SB of the bottom Nt. The one side part-apex imaging camera 51 (SS(Na)) corresponds to the apex SS of one side part Na. The other side part-apex imaging camera 51 (SS(Nb)) corresponds to the apex SS of the side part Nb of the other side part of the notch N.

Further, a notch illumination part 52 illuminates the notch N. The notch illumination part 52 is provided with an aggregate of optical diodes that illuminates the illumination light to the notch N. Each imaging camera 51 is installed in an install bed 53 so that the illumination light from the notch illumination part 52 positioned in a bright field of a reflected light.

Figure 2:
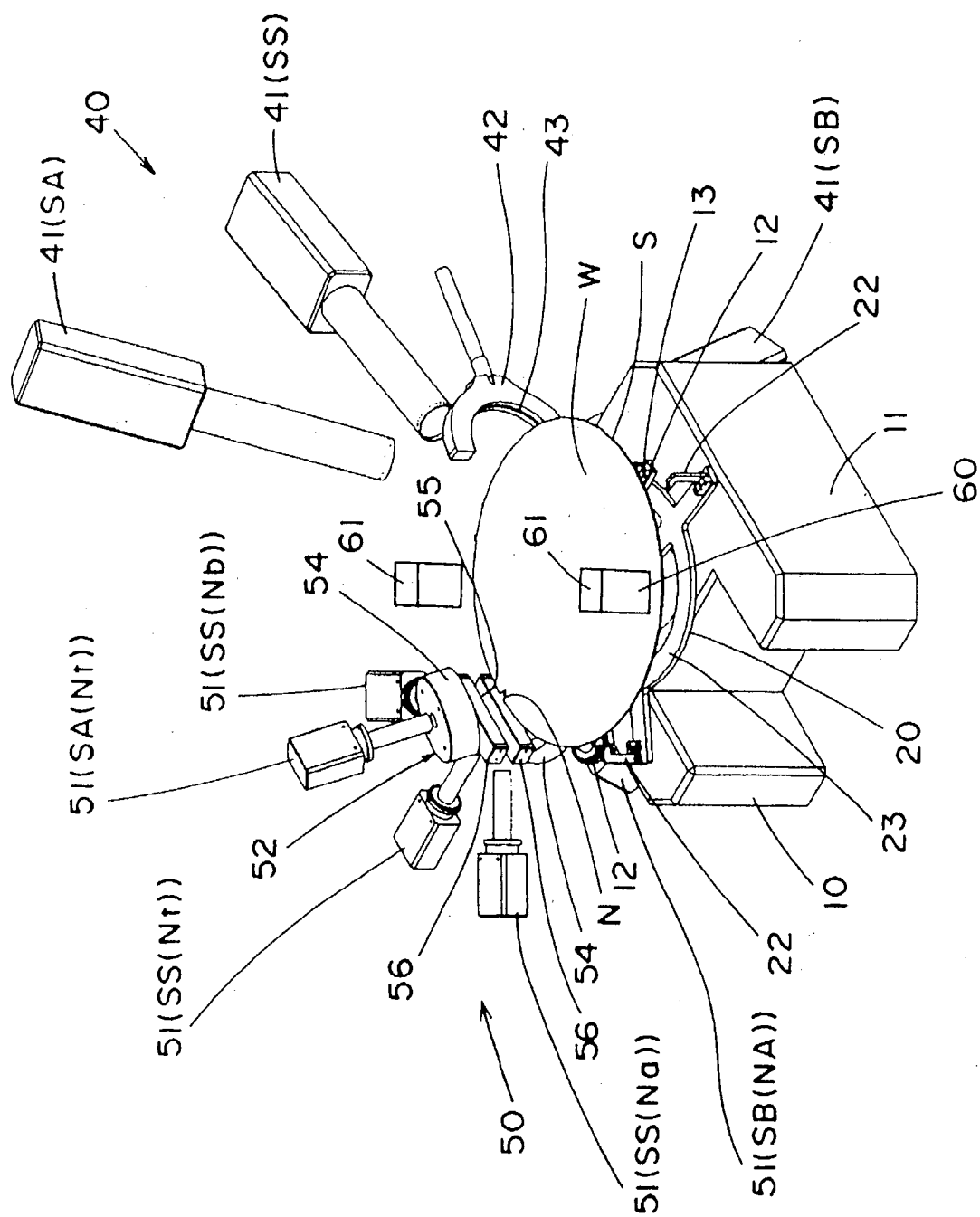
FIG. 2 is a main perspective view showing a wafer inspection apparatus according to the present invention.
Figure 3:
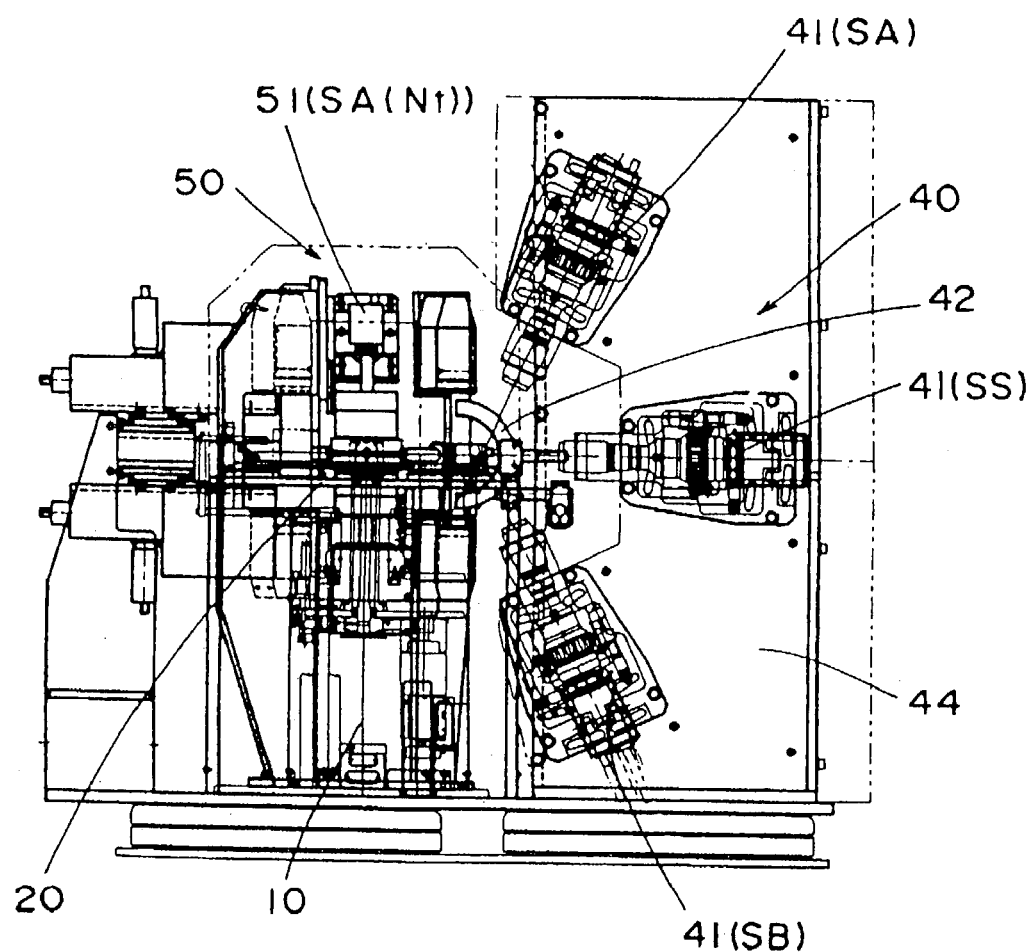
FIG. 3 is a front view showing a wafer inspection apparatus according to the present invention.
Figure 4:
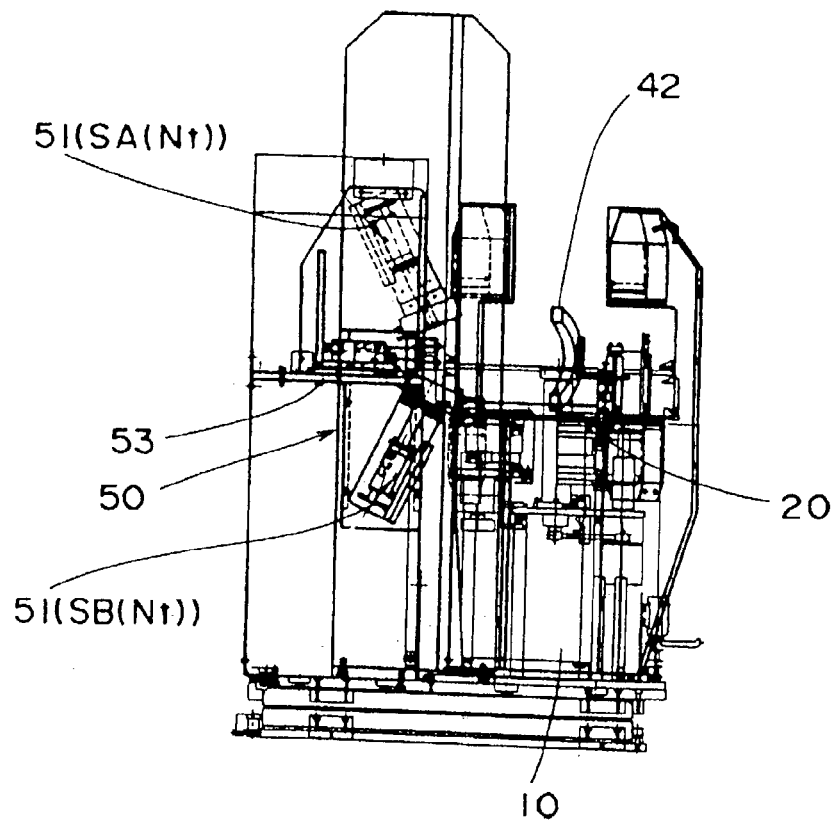
FIG. 4 is a left side view showing a wafer inspection apparatus according to the present invention.
Figure 5:
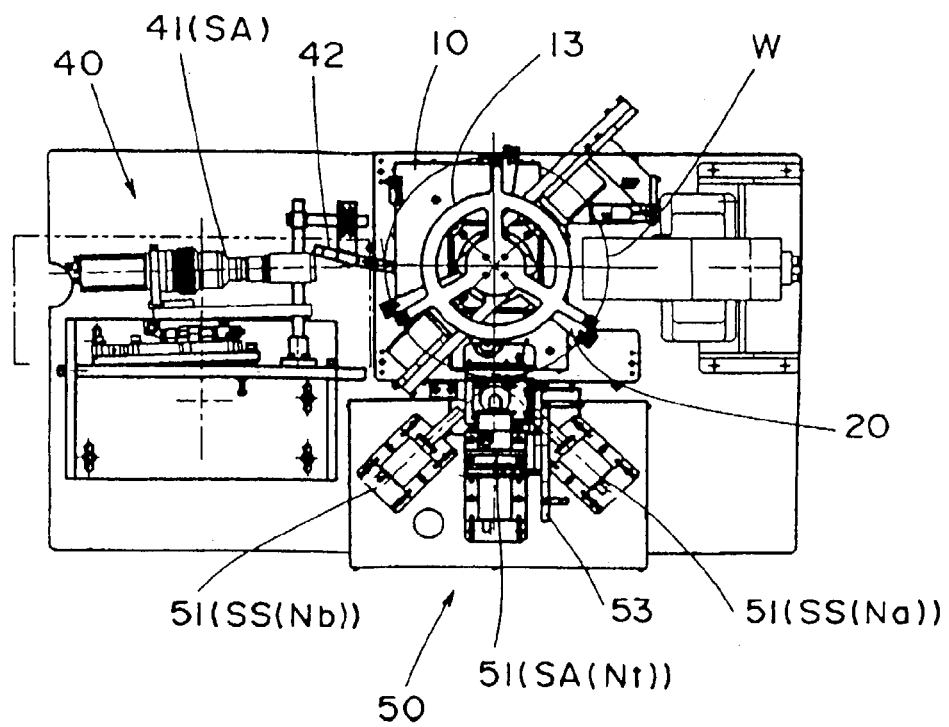
FIG. 5 is a plane view showing a wafer inspection apparatus according to the present invention.
Figure 6:
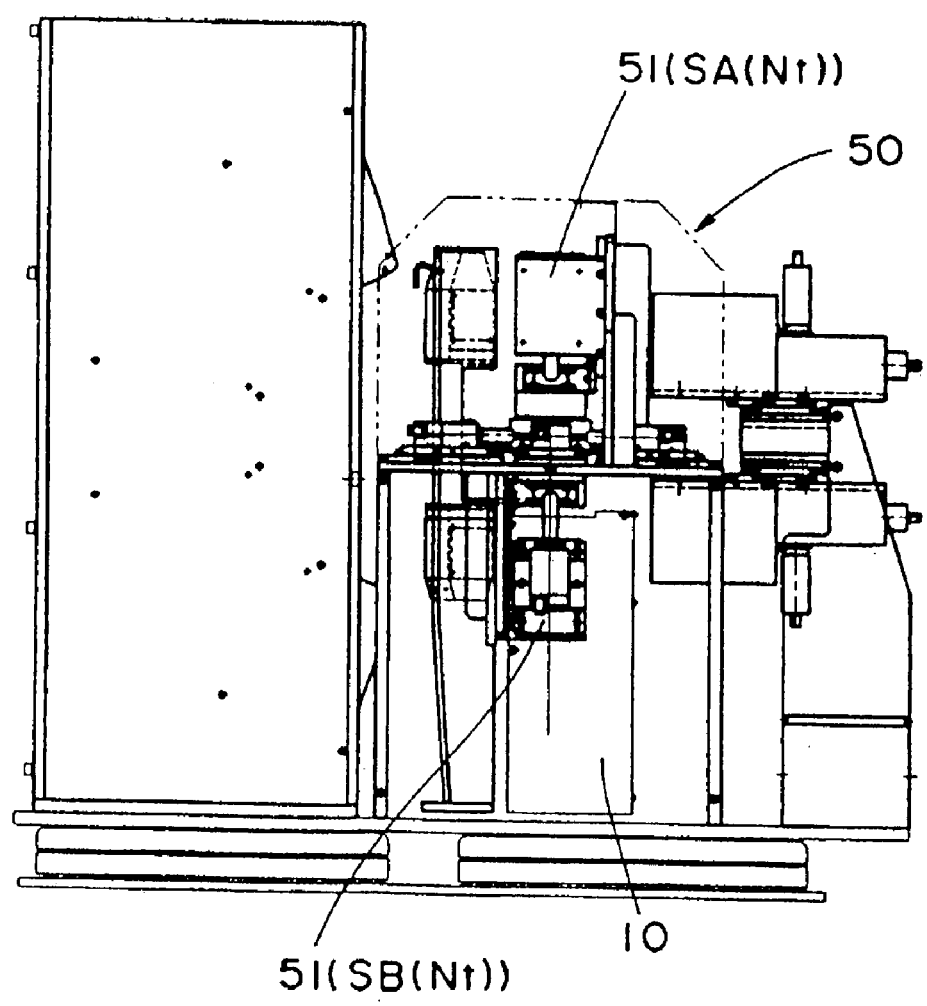
FIG. 6 is a rear view showing a wafer inspection apparatus according to the present invention.

As shown in FIG. 2, the notch illumination part 52 has dome illumination bodies 54 and flat illumination bodies 56. Dome illumination bodies 54 are provided with the bottom front side bevel imaging camera 51 (SA(Nt)) and the bottom back side bevel imaging camera 51 (SB(Nt)) for illuminating the illumination light to the notch N. Each imaging face of the imaging camera 51 forms a dome-like illumination face facing centrally. The flat illumination bodies 56 have a pair of substantially flat illuminating faces provided so as to form a slit 55 for illuminating the illumination light to the notch N. At the slit 55, the imaging faces of the bottom apex imaging camera 51 (SS(Nt)), one side part-apex imaging camera 51 (SS(Na)) and the other side part-apex imaging camera 51 (SS(Nb)) are facing.

As an optical system to image the notch N, diffusion illuminations and area cameras are used. These are the same optical system with a general photography.

Figure 29:
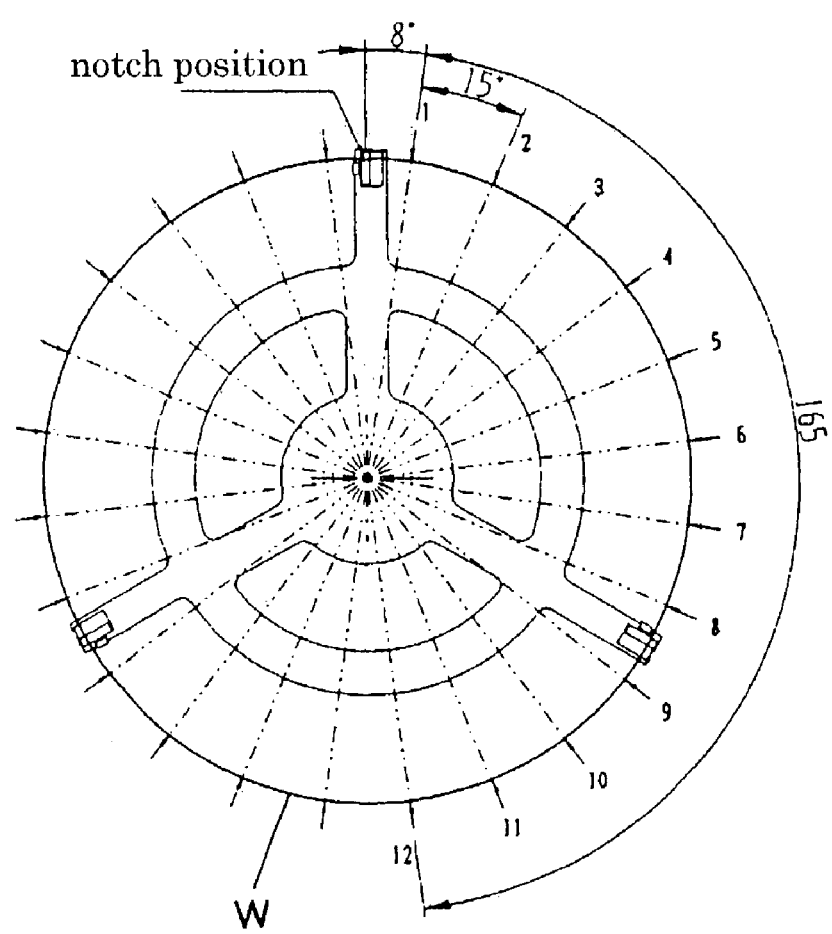
FIG. 29 shows a measuring method for a wafer of a diameter measuring part of a wafer inspection apparatus according to the present invention.

A diameter measuring means 60 for measuring the diameter of the wafer W comprises a pair of optical sensors 61. The optical sensors 61 are provided in a phase shift of 180° each other to be opposed, and detect the position of the circumferential edge S of the wafer W. As shown in FIG. 29, measurement starts from a position rotated about 8° from the notch N at every 15°. Then, for example, the diameter of the wafer W is measured in fixed-point value of 7-digit of a millimeter unit.

Next, the control means 70 is explained.

Figure 1:
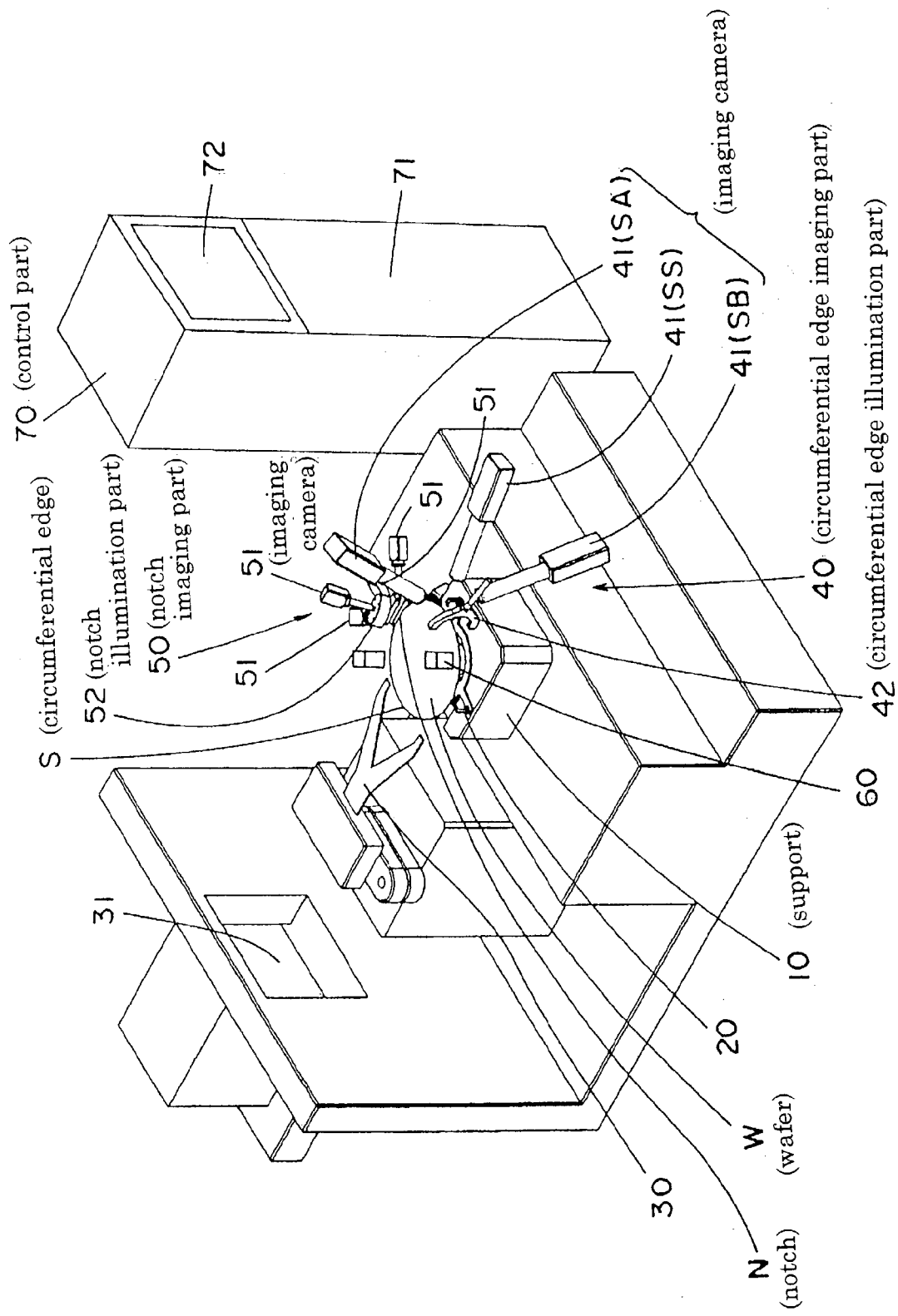
FIG. 1 is a perspective view showing a wafer inspection apparatus according to the present invention.

As shown in FIG. 1, the control means 70 includes an image data processing means 71 and a display 72 such as CRT.

Figure 17:
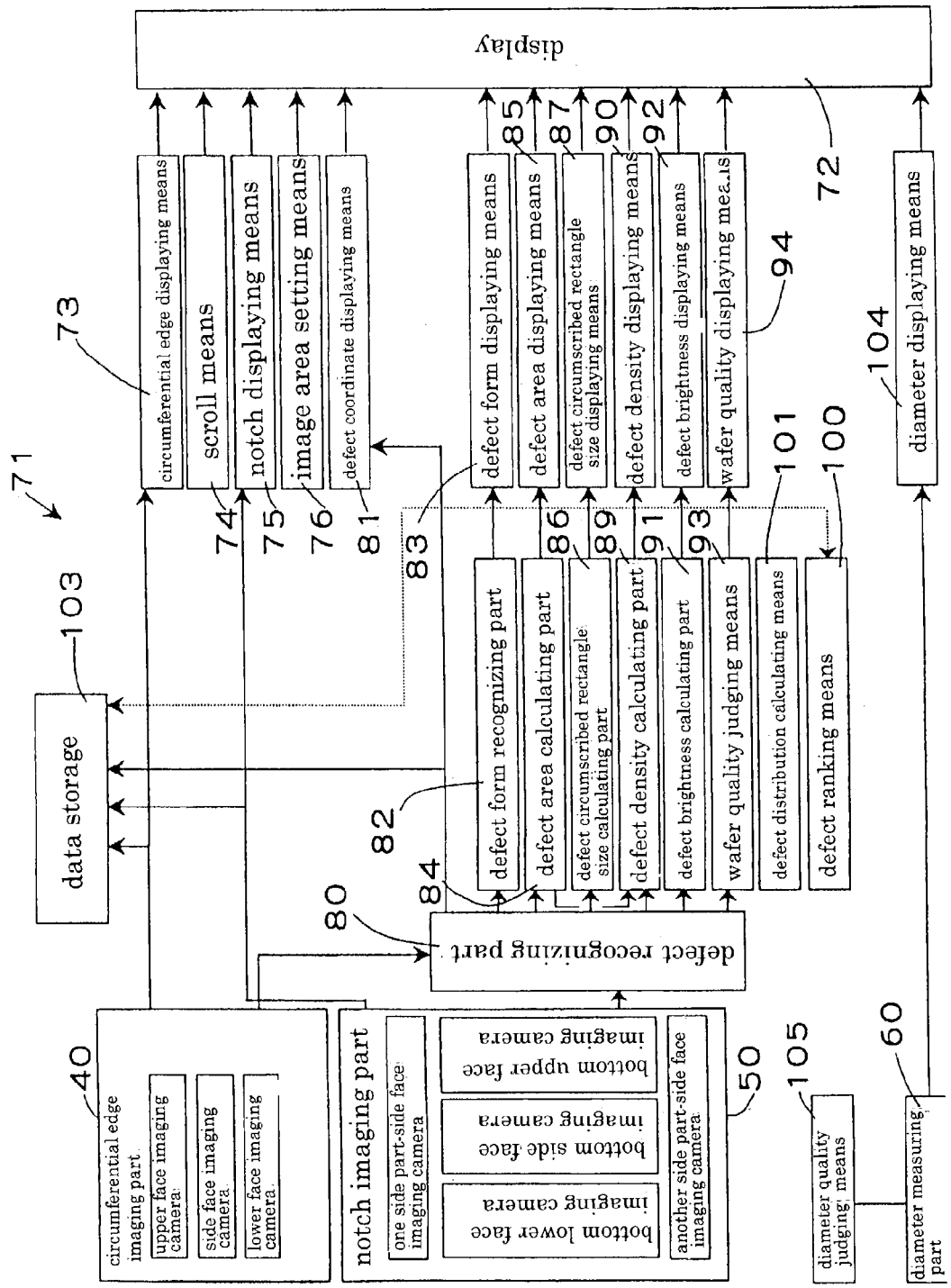
FIG. 17 is a block diagram showing a constitution of an imaging data processing means of a control means of a wafer inspection apparatus according to the present invention.
Figure 18:
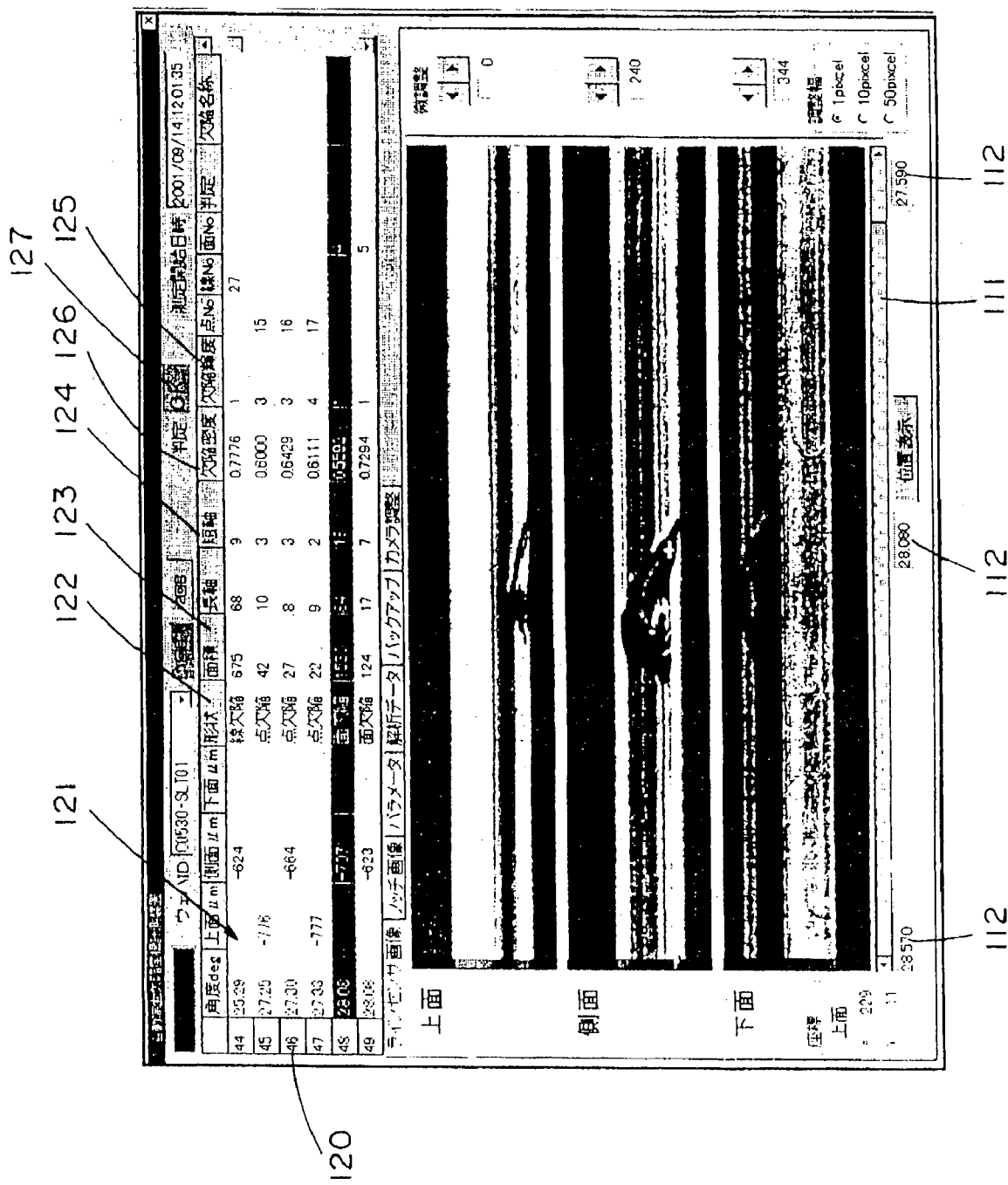
FIG. 18 shows an imaging data indication display of a circumferential edge by a display of a wafer inspection apparatus according to the present invention.

The image data processing means 71 is provided with, as shown in FIG. 17, a circumferential edge displaying means 73. The circumferential edge displaying means 73 simultaneously displays the circumferential edges S of the wafer W imaged by the plurality of imaging cameras 41 of the circumferential edge imaging means 40 in such a condition that each phase of the angle positions is matched. FIG. 18 shows one example displayed by the display 72.

In detail, if the imaging cameras 41 (line sensor) obtain, for example, an image of about 3300 μm width in 1024 pixels, an image of 304 pixels (about 1000 μm width) are cutout from the image to display.

Further, the image data processing means 71 has a scroll means 74 for scrolling images of the circumferential edge S of the wafer W displayed by the circumferential edge displaying means 73 along the peripheral direction of the circumferential edge S of the wafer W. Thus, as shown in FIG. 18, the images of the circumferential edge S of the wafer W scroll.

Further, the image data processing means 71 has a notch displaying means 75 for simultaneously displaying images of the notch N on the display 72, which is imaged by the plurality of imaging cameras 51 in the notch imaging means 50.

Figure 19:
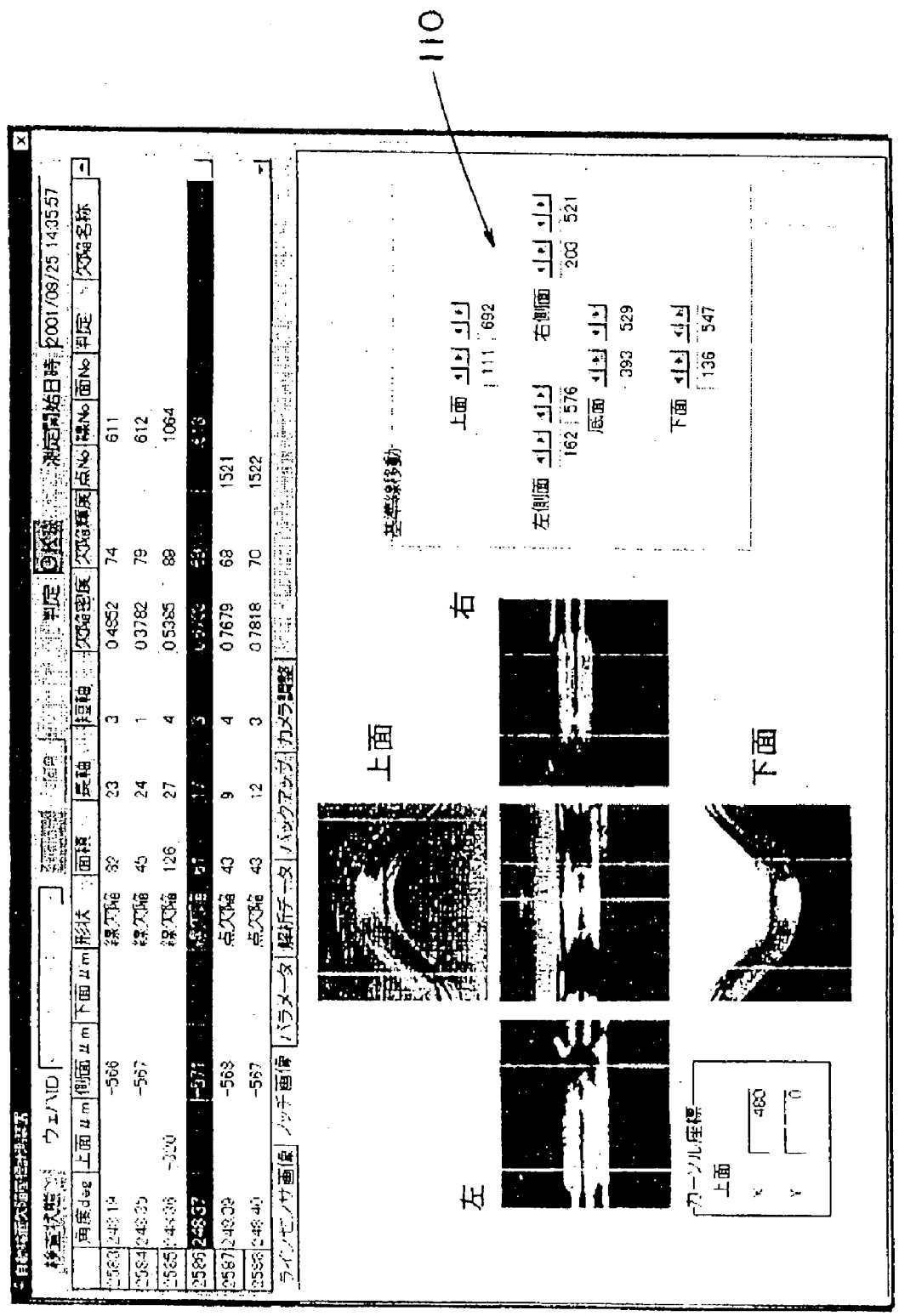
FIG. 19 shows an imaging data display screen of a notch on a display of a wafer inspection apparatus according to the present invention.

FIG. 19 shows one example of such a display screen.

The image data processing means 71 is provided with an image area setting means 76 for setting an optimum imaging area for the image of the notch N, which corresponds to each imaging camera 51 and is displayed on the display 72 on the basis of a reference position.

Figure 20:
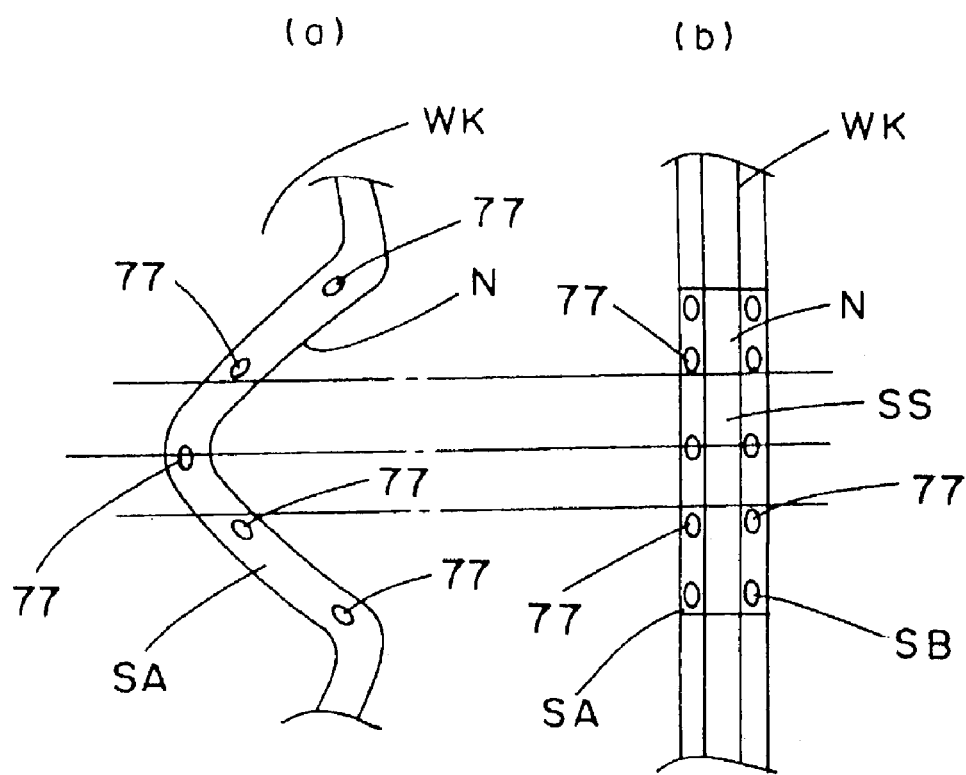
FIG. 20(a) is a front view of a notch showing a reference wafer for adjusting a position of an image of a notch of a wafer inspection apparatus according to the present invention.
FIG. 20(b) is a front view of the notch.
Figure 21:
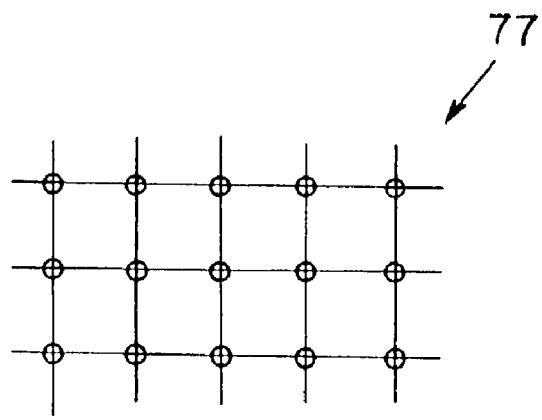
FIG. 21 shows matrix points attached to a reference wafer for adjusting a position of an image of a notch of a wafer inspection apparatus according to the present invention.

As shown in FIG. 20 and FIG. 21, the reference position is set by means of a reference wafer WK. On the front side bevel SA and the back side bevel SB of the notch N of the reference wafer WK, position-distinguishing marks 77 are put on certain positions. The position-distinguishing marks 77 are set by visual observation of the display. Area setting is done based on where the image of the notch N is focused by the imaging camera 51 (area sensor). Area setting is not done where the image is not focused.

Further, the image data processing means 71 is provided with a defect recognizing means 80 and a defect coordinate displaying means 81. The defect recognizing means 80 recognizes an area as a defect, the area having a difference of brightness relative to a standard brightness to be based from the image data of the circumferential edge S of the wafer W and the image data of the notch N. The defect coordinate displaying means 81 displays a coordinate of the defect identified by the defect recognizing means 80 on the display 72.

The defect coordinate displaying means 81 has an angle coordinate display function and a thickness direction coordinate display function. The angle coordinate display function is to display an angle coordinate along the peripheral direction regarding the circumferential edge S of the wafer W. The thickness direction coordinate display function is to display a relative position along the thickness direction of the circumferential edge S of the wafer W.

In detail, if the line sensor scans, for example, an image of 1024 pixels and about 3300 μm width, defect detection is done by cutting out 304 pixels (about 1000 μm width) from the image. Further, the reference position (0 position) of the coordinate of the defect is set relative to the image cutout.

Further, the defect coordinate displaying means 81 sets a reference position at each screen for the notch N. The position of the defect is displayed from the reference position. In detail, the reference position is set by the number of pixels from upper left side of the screen. The coordinate of defect displays the reference position as the origin.

Figure 22:
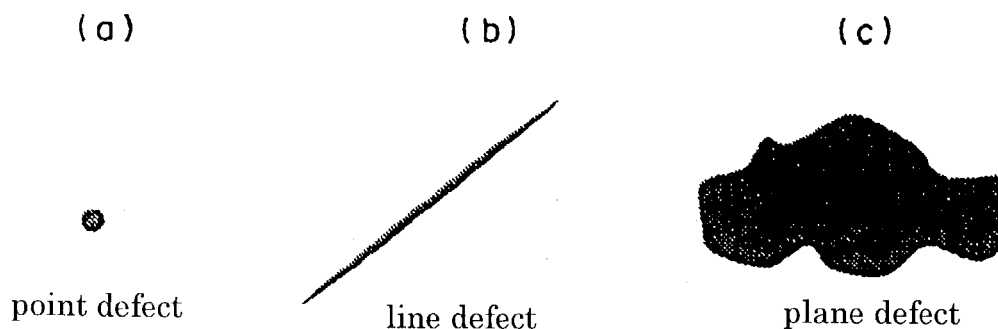
FIG. 22(a) shows point defects as a mode of defects identified by a defect form recognizing means of a wafer inspection apparatus according to the present invention.
FIG. 22(b) shows line defects thereof.
FIG. 22(c) shows plane defects thereof.

Further, the image data processing means 71 is provided with a defect form recognizing means 82 and a defect form displaying means 83. The defect form recognizing means 82 recognizes the defect form identified by the defect recognizing means 80. The defect form displaying means 83 displays the form identified by the defect form recognizing means 82 on the display 72. The defect form recognizing means 82 has, as shown in FIG. 22, a function of classifying into one of point defects, line defects, and plane defect and recognizing based on a predetermined threshold value.

Figure 23:
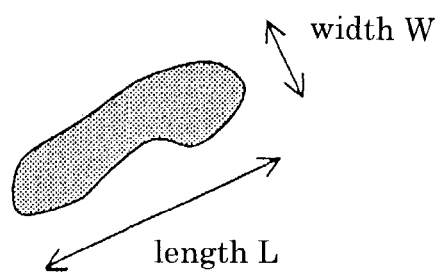
FIG. 23 shows a method for judging line defects to be identified by a defect form recognizing means of a wafer inspection apparatus according to the present invention.

As shown in FIG. 23, when classifying defects, if a ratio of the length and the width is larger than a certain value, it is considered to be a line defect. If the ratio is smaller than the certain value, it is considered to be a plane defect.

The image data processing means 71 is provided with a defect area calculating means 84, a defect area displaying means 85, a defect circumscribed rectangle size calculating means 86, and a defect circumscribed rectangle size displaying means 87. The defect area calculating means 84 obtains an area of the defect identified by the defect recognizing means 80. The defect area displaying means 85 displays the area calculated by the defect area calculating means 84. The defect circumscribed rectangle size calculating means 86 obtains the size of the rectangle circumscribing the defect that is recognized by the defect recognizing means 80. The defect circumscribed rectangle size displaying means 87 displays the size calculated by the defect circumscribed rectangle size calculating means 86 on the display 72.

The image data processing means 71 is provided with a defect density calculating means 89 and a defect density displaying means 90. The defect density calculating means 89 obtains the density of the defect (from the area of the defect calculated by the defect area calculating means 84 and from the size of the circumscribed rectangle calculated by the defect circumscribed rectangle size calculating means 86). The defect density displaying means 90 displays the density of the defect calculated by the defect density calculating means 89.

The image data processing means 71 is provided with a defect brightness calculating means 91 and a defect brightness displaying means 92. The defect brightness calculating means 91 obtains a mean brightness of the defect identified by the defect recognizing means 80. The defect brightness displaying means 92 displays a mean brightness calculated by the defect brightness calculating means 91 on the display 72.

On the display 72, as shown in FIG. 18 and FIG. 19, information of the defect on the wafer W is displayed as follows.

(1) defect position (120 in FIG. 18)

Position of center of gravity of the defect form is displayed.

(2) defect coordinate (121 in FIG. 18)

(3) kind of defect (122 in FIG. 18)

Defects detected are classified as follows.

Line defects: one in which the length and width are largely different (a ratio of the length and width is set for judgment)

Plane defects: one in which the area is large

Point defects: one except for line defects or plane defects (4) Picture element of area defects (123 in FIG. 18)

(5) Length of the major axis, length of the minor axis (124 in FIG. 18)

A rough length and width of the defect form are displayed. These are obtained from the circumferential length P of the defect form and area A by holding the next equation.

When the length and the width of the form is L and W, respectively, the circumferential length P becomes P=2*(L+W). The area A becomes A=L*W.

(6) Brightness of defect (125 in FIG. 18)

It expresses a brightness value. The brightness value means a mean brightness of the defect.

(7) Density of defect (126 in FIG. 18)

It expresses a ratio of an area of the circumscribed rectangle of the detected defect and an area of the defect.

Further, the image data processing means 71 is provided with a wafer quality judging means 93 and a wafer quality displaying means 94. The wafer quality judging means 93 judges quality of the wafer W based on the defect identified by the defect recognizing means 80. The wafer quality displaying means 94 displays quality of the wafer W judged by the wafer quality judging means 93 on the display 72. Predetermined conditions of the defect, for example the number of the defects, the size of the defects etc. are compared with the real inspection result. If it is in a permissible range, it is recognized to be good. If it is out of the permissible range, it is recognized to be bad. Judged results of "OK" or "NO" are displayed on the display column of the display screen (FIG. 18).

Further, the image data processing means 71 is provided with a defect ranking means 100. The defect ranking means 100 ranks a size degree of point defects, line defects, and plane defects by certain angles based on the calculated data of the many kinds of defects at each image of the circumferential part of the wafer W by each imaging camera 41.

As a table shown in the FIG. 25, for example, the number of defects that are ranked into various kinds at each measuring face is obtained for ranking by an area of each defect. Maximum value of area is set to a set value of each rank in advance. It is constituted that rank can be set in a range from 1 to 10, for example. The rank 1 expresses distribution of large defects, while the rank 10 expresses distribution of small defects.

Further, the image data processing means 71 is provided with a defect distribution calculating means 101 for calculating distribution of point defects, line defects, and plane defects at certain unit of angles on the image face of each imaging camera 41 of the circumference of the wafer W. As shown in FIG. 26, distribution of the number at the position of the defect is obtained at each unit of set angles for each rank. The set angles are set to 10°, 15°, 30°, 45°, 60°, and 90°, for example. Distribution expresses the number of designated angles. For example, when 10° unit is set, a column 90° shows the number of 80°~90°. FIG. 26 is an example that 10° unit is set.

Figure 27:
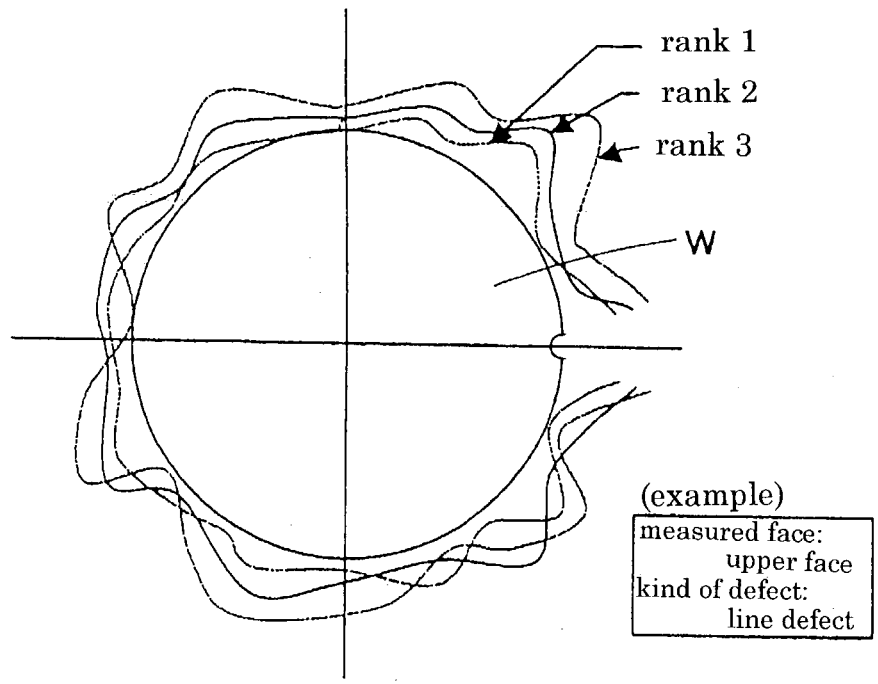
FIG. 27 shows an example displaying a result of a defect ranking means and a defect distribution calculating means of a wafer inspection apparatus according to the present invention in relation to a wafer.
Figure 28:
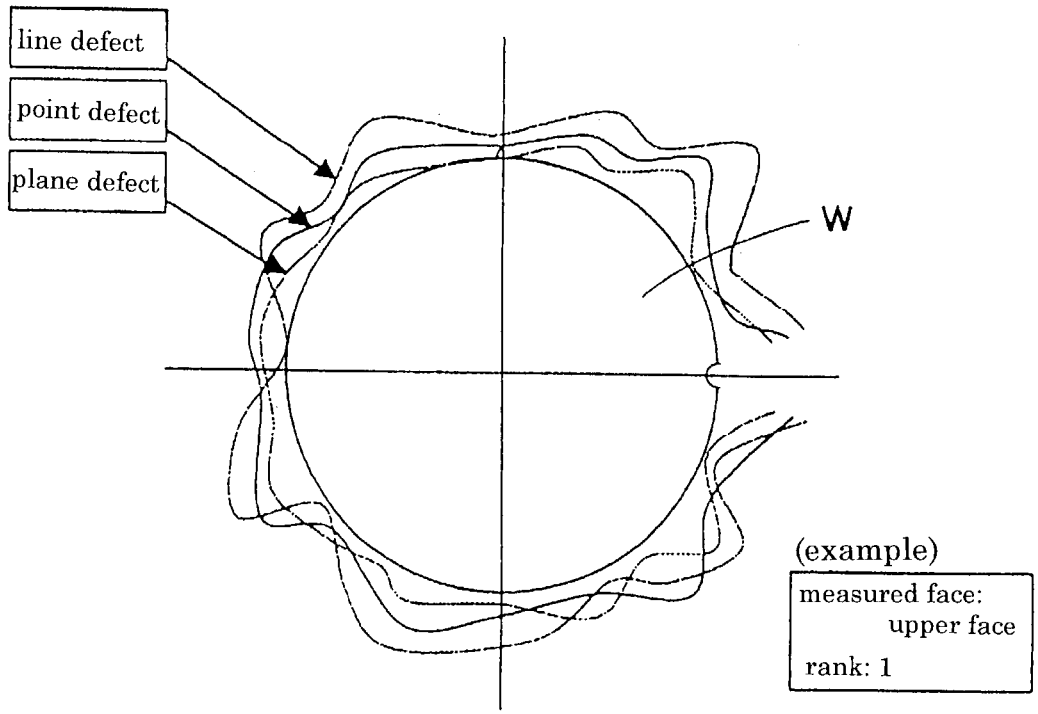
FIG. 28 shows another example displaying a result of a defect ranking means and defect distribution calculating means of a wafer inspection apparatus according to the present invention in relation to a wafer.

Then, the control means 70 is constituted so that a table as shown in FIG. 27 and FIG. 28 can be output by means of the display 72 or a printer, for example, based on the result of these defect ranking means 100 and defect distribution calculating means 101.

FIG. 27 shows a distribution of the number of defects at each rank by designating a measuring face and a defect type.

FIG. 28 shows the number-distribution of each defect type by designating a measuring face and a rank. Thus, the wafer condition is easily expressed by displaying frequency distribution on the circumference. Because the condition or size degree of the defects on the circumferential edge S is clear, it can be utilized for solution of defect generation. Accuracy of inspection is improved.

Figure 32:
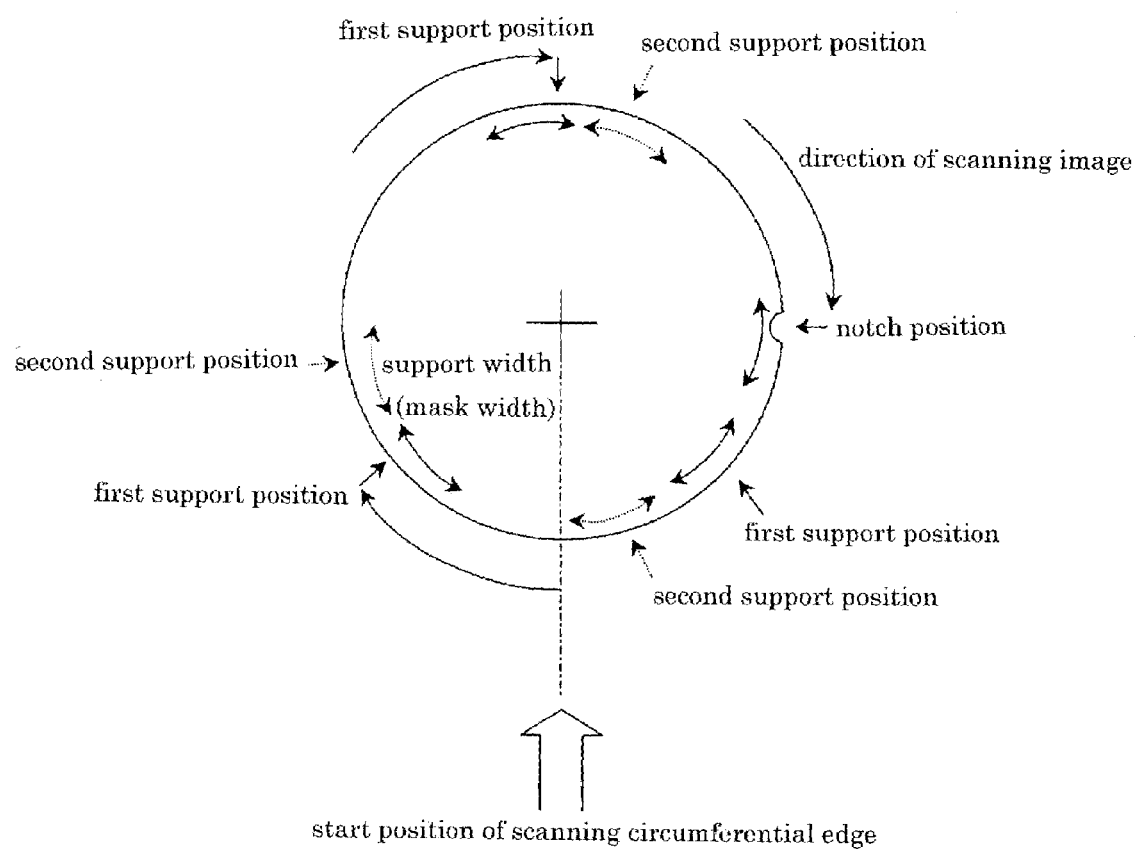
FIG. 32 shows a state of a support position of a wafer by a supporting means of a wafer inspection apparatus according to the present invention.

In the image data processing means 71, as shown in FIG. 32, parts that correspond to the notch N and the support finger 12 of the supporting board 13 are masked so that the parts are not processed of defect detection. Therefore, the support position changing system 20 is constituted to support the wafer W again to expose and image the parts that could not be imaged and hindered by the support fingers 12. Therefore, the image data for one circumference of the wafer W is obtained for two times. The foregoing display and process of defect information is done at each image data.

Further, the image data processing means 71 has a data storage means 103 for memorizing and storing the image data imaged by each imaging camera 41, 51 or a result calculated by each calculating means by corresponding ID number of the wafer inspected. The wafer W to be inspected has its own ID number. Each data is memorized based on the ID number by reading the ID number with a reading sensor (not shown). The data can be output to the printer etc. by reading them from the data storage means 103 as the need arises.

Further, the control means 70 is provided with a diameter displaying means 104 for displaying the diameter measured by the diameter measuring means 60 by corresponding the ID number. As shown in FIG. 29, measurement is started where the measuring point is rotated about 8° from the position of the notch N. Measurement is done at every 15°. For example, the diameter of the wafer W is measured in fixed-point value of 7-digit of a millimeter unit.

The control means 70 a diameter quality judging means 105. If it is in a permissible range, it is recognized to be good. If it is out of the permissible range, it is recognized to be bad. Judged results are displayed on the display 72 (not shown).

When the image is displayed on the display 72, the image can be enlarged on the display.

According to the wafer inspection apparatus of the embodiment, the image of the imaging camera 51 is adjusted in advance. Particularly, the notch image shown in FIG. 19 is adjusted.

Figure 30:
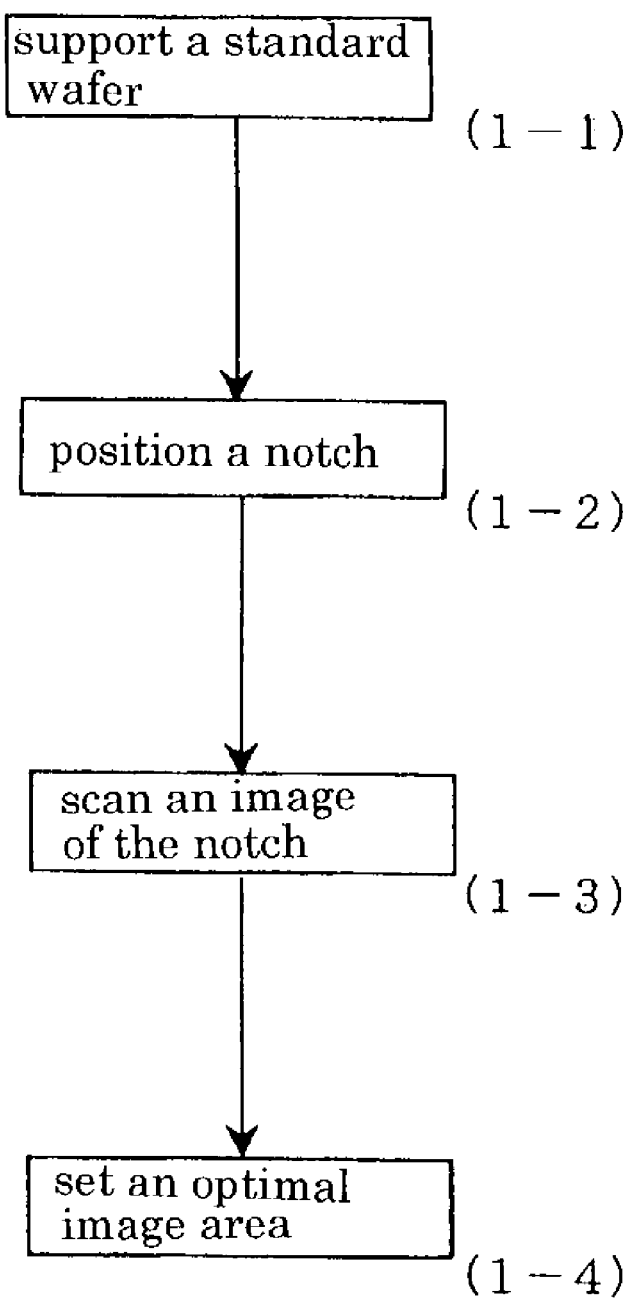
FIG. 30 is a flowchart showing a procedure on adjusting image of a notch of a wafer inspection apparatus according to the present invention.

A flowchart shown in FIG. 30 is explained.

By means of the wafer transfer 30, the supporting means 10 supports the reference wafer WK (1-1). The supporting board 13 is rotated to move the notch N to the position for imaging by the notch imaging means 50 and the notch N is positioned (1-2). The image of the notch N is obtained by the notch imaging means 50 (1-3). Display is enlarged on the display 72. The part focused on the notch N is matched the matrix points of the position distinguishing mark 77 put on the reference wafer WK shown in FIG. 20 and FIG. 21 by visual observation. In accordance with the position of the points, as shown in FIG. 19, the optimum area is set by an area setting part 110 (1-4). In this case, the area can be precisely adjusted by means of the matrix points. Area setting is done reliably. Thus, the image data is processed based on the image by setting the area. Therefore, it can recognize the defect with better accuracy.

Next, when the wafer W is inspected by using the wafer inspection apparatus thus adjusted, the process is as follows.

Figure 10:
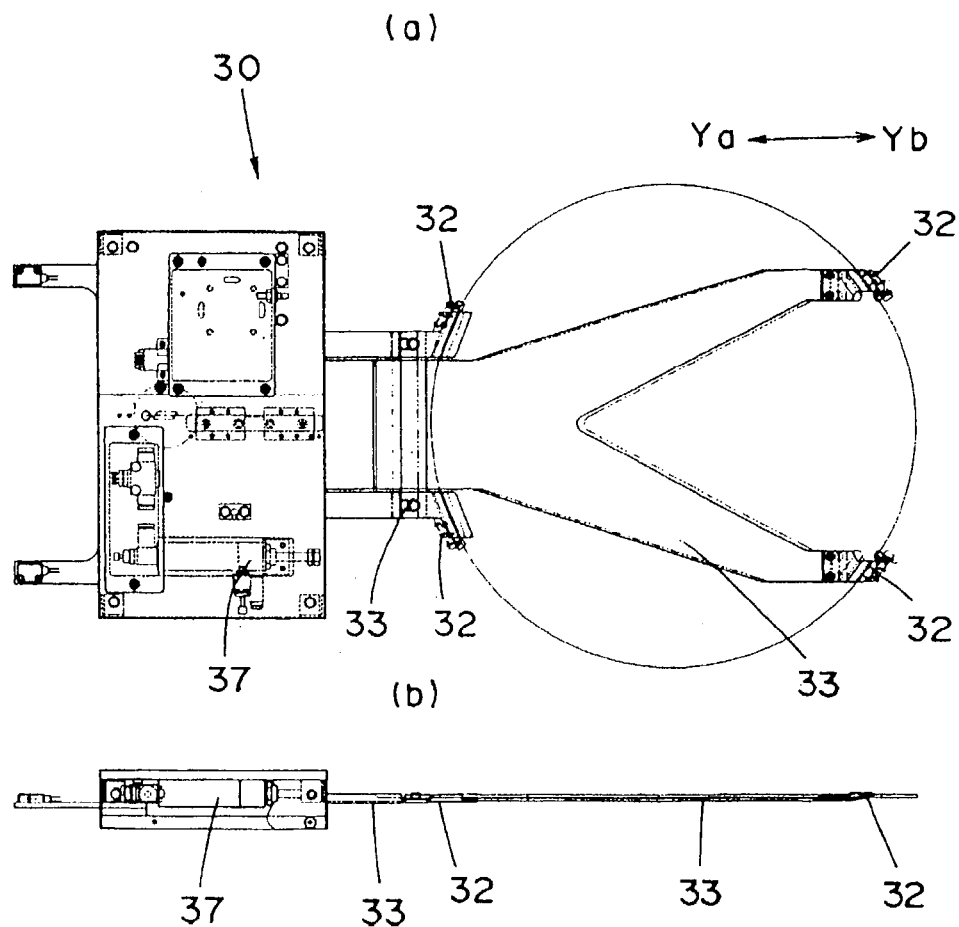
FIG. 10($a$) is a plane view showing a wafer transfer of a wafer inspection apparatus according to the present invention.

Firstly, the wafer W is transferred to the supporting means 10 (2-1). This transfer is done by taking out of the wafer W to be inspected with the carrying hands 33 from the storage 31 for the wafer W by the wafer transfer 30. Now, at the position for taking out of the storage 31, as shown in FIG. 10 and FIG. 11, the carrying hands 33 are positioned in the carrying position Ya. The engaging means 32 engage the circumferential edge S of the wafer W. The wafer W is carried and grasped in the face direction of the wafer W. As shown in FIG. 11, the abutting members 36a of the engaging means are elastically contacted by elasticity of the plate spring 36b. Therefore, the wafer W becomes centripetal. The wafer W is centered relative to the support fingers 12 of the supporting board 13 of the supporting means 10.

As shown in FIG. 1 and FIG. 2, FIG. 7 and FIG. 9, FIG. 33(*a*), the wafer W is transferred to the supporting board 13 of the supporting means 10. The carrying hands 33 are positioned at a certain position to the release position Yb. The wafer W is released and supported by the supporting board 13 (2-2). In this case, because the wafer W is centered relative to the support fingers 12 of the supporting board 13, accuracy becomes high regarding positioning the wafer W relative to the supporting board 13. Accuracy of inspection thereafter is improved accordingly. Further, because the wafer W is supported by the support fingers 12 and supported on a line of an inclined support face 17 of the support fingers 12, bad influence such as damaging the face of the wafer W is avoided.

Next, as shown in FIG. 32, the notch N is positioned by moving the notch N to where the notch imaging means 50 images by rotating the supporting board 13 (2-3). In this state, ID number of the wafer W is read by the reading sensor (not shown) (2-4). The image of the notch N is obtained by the notch imaging means 50 (2-5). The image data obtained is sent out to the image data processing means 50 and processed (2-6) by a graphical processor.

The notch imaging means 50 has the imaging cameras 51. The imaging cameras 51 correspond to the apex SS, the front side bevel SA, and back side bevel SB, and are positioned so that each imaging direction will be at right angles to the face. The notch imaging means 51 has a bottom apex imaging camera 51 (SS(Nt)), a bottom front side bevel imaging camera 51 (SA(Nt)), a bottom back side bevel imaging camera 51 (SB(Nt)), one side part-apex imaging camera 51 (SS(Na)), and the other side part-apex imaging camera 51 (SS(Nb)). The bottom apex imaging camera 51 (SS(Nt)) corresponds to the apex SS of the bottom Nt of the notch N. The bottom front side bevel imaging camera 51 (SA(Nt)) corresponds to the front side bevel SA of the bottom Nt of the notch N. The bottom back side bevel imaging camera 51 (SB(Nt)) corresponds to the back side bevel SB of the bottom Nt. The one side part-apex imaging camera 51 (SS(Na)) corresponds to the apex SS of one side part Na. The other side part-apex imaging camera 51 (SS(Nb)) corresponds to the apex SS of the side part Nb of the other side part of the notch N. Therefore, even if the notch N is beveled, whole part in the thickness direction can be imaged clearly and simultaneously, without moving the position of the imaging cameras 51 one by one. Operation of imaging the edge faces is improved. Accuracy for imaging is improved accordingly.

Further, because the imaging cameras 51 are constituted of area sensors, they can image at one time without rotating the wafer W.

The notch illumination part 52 illuminates the notch N. The notch illumination part 52 is provided with the dome illumination bodies 54 and flat illumination bodies 56 to illuminate the notch N. Each imaging camera 51 is positioned so as to position in the bright field of the reflected light from the illumination light of the notch illumination part 52. Therefore, each face of the notch N can be imaged clearly. Particularly, the defects can be imaged well. Also regarding the point, accuracy of image is improved accordingly.

When imaging the notch N of the wafer W is ended, the circumferential edge S is imaged next. Firstly, the wafer W is rotated (2-7), the image of the circumferential edge S is obtained by the circumferential edge imaging means 40 (2-8). The image data obtained is sent out to the image data processing means 71 and processed (2-9) by a graphical processor.

In the image data processing means 71, as shown in FIG. 32, the masks are set on the parts of the notch N and the support fingers 12 of the support finger 13. These parts are not processed for defect-detection.

The circumferential edge imaging means 40 is provided with, as shown in FIG. 1, FIG. 2, FIG. 14 to FIG. 16, the imaging camera for an apex 41 (SS), the imaging camera for a front side bevel 41 (SA), and the imaging camera for back side bevel 41 (SB). Each camera is positioned such that the imaging directions are at right angles to each face. Therefore, even if the circumferential edge S of the wafer W is beveled, whole part in the thickness direction can be imaged clearly and simultaneously, without moving the position of the imaging cameras 41 one by one. Operation of imaging the edge faces is improved. Accuracy for imaging is improved accordingly.

Further, because the imaging cameras 41 are line sensors, the circumferential edge S is imaged with narrow width and continued. Therefore, resolution of edge images becomes good. Accuracy of imaging is also improved accordingly.

The circumferential edge illumination part 42 illuminates the circumferential edge S. The circumferential edge illumination part 42 forms the illumination face along the certain arc along the thickness direction of the circumferential edge S of the wafer W and illuminates the illumination light so as to focus on the center of the arc. Each imaging camera 41 is positioned so that the illumination light from the circumferential edge illumination part 42 is positioned in the bright field of the reflected light. In other word, each imaging camera 41 is positioned so as to receive the illumination from the C-shape circumferential edge illumination part 42 in regular reflection. Therefore, each face of the circumferential edge S can be imaged clearly. Particularly, defects can be imaged well. Accuracy of imaging is improved accordingly.

Figure 33:
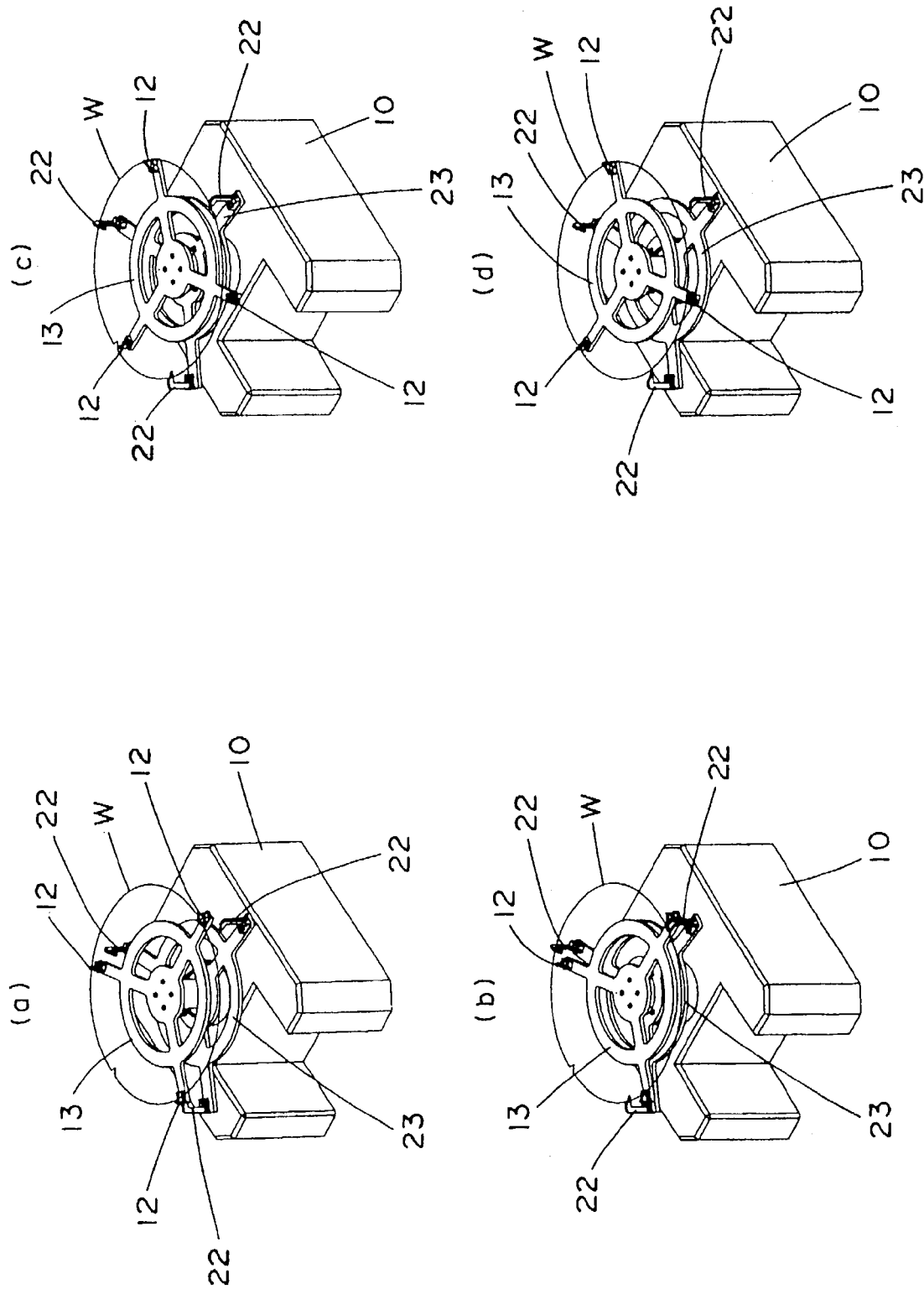
FIGS. 33a–33d are process drawings showing a state of a wafer inspection apparatus according to the present invention.
Figure 34:
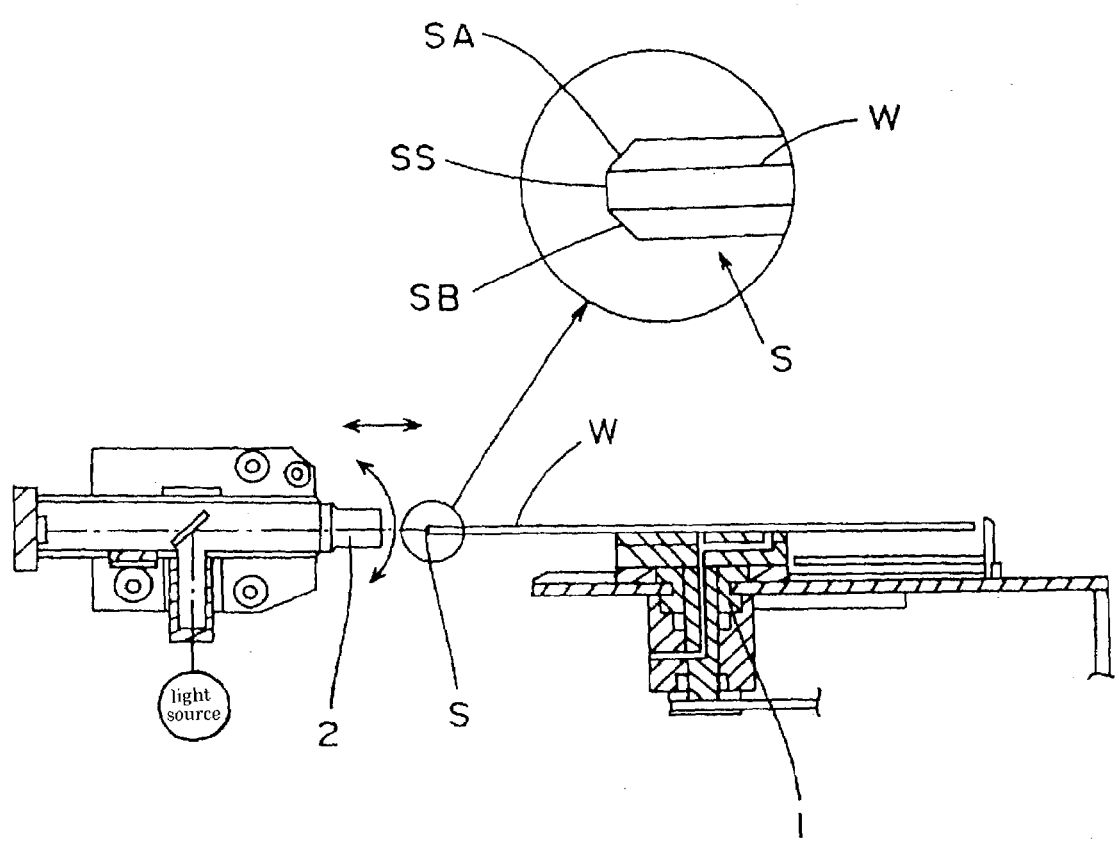
FIG. 34 shows an example of a prior wafer inspection apparatus.

Next, because each imaging camera 41 cannot image the part of the support fingers 12 of the supporting board 13, the support position changing means 20 changes the position of the wafer W that is supported by the support fingers 12 of the supporting board 13 (2-10). This moves, as shown in FIG. 33(*a*), the carrying board 23 at the delivery position Xb to the carrying position Xa, as shown in FIG. 33(*b*). Thus, the wafer W supported by the supporting board 13 is carried and lifted by the carrying fingers 22 of the carrying board 23. As shown in FIG. 33(*c*), during lifting, the support fingers 12 are positioned to the other angle phase position by rotating the supporting board 13. Then, as shown in FIG. 33(*d*), the wafer W is delivered to the support fingers 12 by positioning the carrying board 23 to the delivery position Xb. In this case, because the support position is changed, the parts that could not be imaged formerly can be exposed and imaged. Further, because the wafer W is carried and lifted by the carrying fingers 22 of the carrying board 23, bad influence such as damaging the face of the wafer W is avoided.

In this state, the wafer W is rotated again (2-11), the image of the circumferential edge S is obtained by the circumferential edge imaging means 40 (2-12). The image data obtained is sent to the image data processing means 71 and processed. (2-13) by a graphical processor.

In the image data processing means 71, as shown in FIG. 32, the masks are set on the parts of the support fingers 12 of the supporting board 13 of the notch N. These parts are not processed for defect-detection.

The circumferential edge imaging means 40 is provided with, as shown in FIG. 1, FIG. 2, FIG. 14 to FIG. 16, the imaging camera for an apex 41 (SS), the imaging camera for a front side bevel 41 (SA), and the imaging camera for back side bevel 41 (SB). Each camera is positioned such that the imaging directions are at right angles to each face. Therefore, even if the circumferential edge S of the wafer W is beveled, whole part in the thickness direction can be imaged clearly and simultaneously, without moving the position of the imaging cameras 41 one by one. Operation of imaging the edge faces is improved. Accuracy for imaging is improved accordingly.

The circumferential edge illumination part 42 illuminates the circumferential edge S. The circumferential edge illumination part 42 forms the illumination face along the certain arc along the thickness direction of the circumferential edge S of the wafer W and illuminates the illumination light so as to focus on the center of the arc. Each imaging camera 41 is positioned so that the illumination light from the circumferential edge illumination part 42 is positioned in the bright field of the reflected light. In other word, each imaging camera 41 is positioned so as to receive the illumination part from the C-shape circumferential edge illumination part 42 in regular reflection. Therefore, each face of the circumferential edge S can be imaged clearly. Particularly, defects can be imaged well. Accuracy of imaging is improved accordingly.

The diameter of the wafer W is measured by the diameter measuring means 60 (2-15). As shown in FIG. 29, the diameter measuring means 60 measures the diameter from the position of the detected circumferential edge S by detecting the position of the circumferential edge S of the wafer W by one pair of optical sensors provided oppositely each other. Measurement starts from the position rotated about 8° from the notch N at every 15°. For example, the diameter of the wafer W is measured in fixed-point value of 7-digit of a millimeter unit. Because measurement of the diameter of the wafer W is done simultaneously with measurement of the defects, efficiency of inspection is improved.

After that, the wafer W is taken out and transferred to the storage 31 of the wafer. The wafer W on the supporting board 13 of the supporting means 10 is grasped and taken out by the wafer transfer 30 and transferred to the storage 31.

Again, the wafer W to be inspected next is taken out of the storage 31 for the wafer W by means of the wafer transfer 30, transferred to the supporting means 10, and processed the same as foregoing.

Data processing of the control means 70 is explained.

In the image data processing means 71, as shown in FIG. 17, the defect recognizing means 80 recognizes the area as the defect, the area having difference of brightness relative to the standard brightness to be based from the image data of the circumferential edge S of the wafer W and the image data of the notch N.

Figure 24:
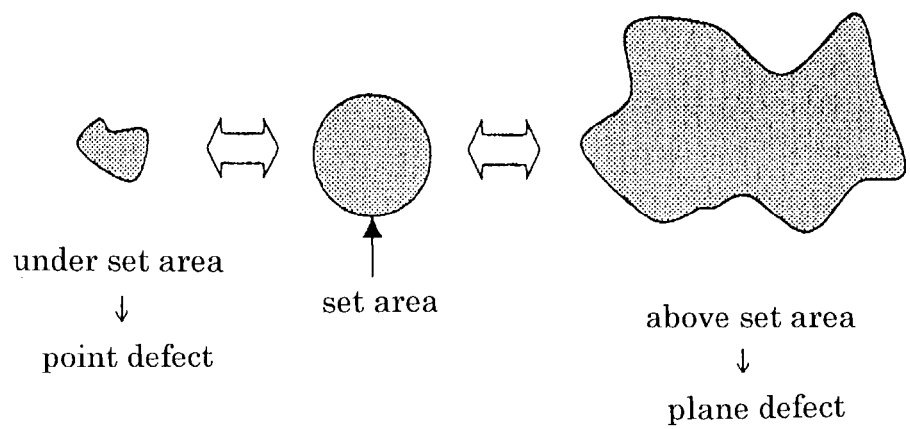
FIG. 24 shows a method for judging point defects and plane defects to be identified by a defect form recognizing means of a wafer inspection apparatus according to the present invention.

Thus, the defect form recognizing means 82 recognizes the form of the defect identified by the defect recognizing means 80. This recognition is done, as shown in FIG. 22 to FIG. 24, by classifying into one of point defects, line defects, and plane defects, based on the predetermined threshold value.

The defect area calculating means 84 obtains an area of the defect identified by the defect recognizing means 80. The defect area displaying means 85 displays the area calculated by the defect area calculating means 84. Based on these, the defect density calculating means 89 obtains the density of the defect from the area of the defect calculated by the defect area calculating means 84 and from the size of the circumscribed rectangle calculated by the defect circumscribed rectangle size calculating means 86.

The defect brightness calculating means 91 obtains a mean brightness of the defect identified by the defect recognizing means 80.

In the image data processing means 71, the wafer quality judging means 93 judges quality of the wafer W based on the defect identified by the defect recognizing means 80. When judging, predetermined conditions of the defect, for example the number of the defects, the size of the defects etc. are compared with the real inspection result. If it is in a permissible range, it is recognized to be good. If it is out of the permissible range, it is recognized to be bad.

The defect ranking means 100 ranks a size degree of point defects, line defects, and plane defects by certain angles based on the calculated data of the many kinds of defects at each image of the circumferential part of the wafer W by each imaging camera 41.

The defect distribution calculating means 101 obtains distribution of point defects, line defects, and plane defects at certain unit of angles on the image face of each imaging camera 41 of the circumference of the wafer W.

Figure 31:
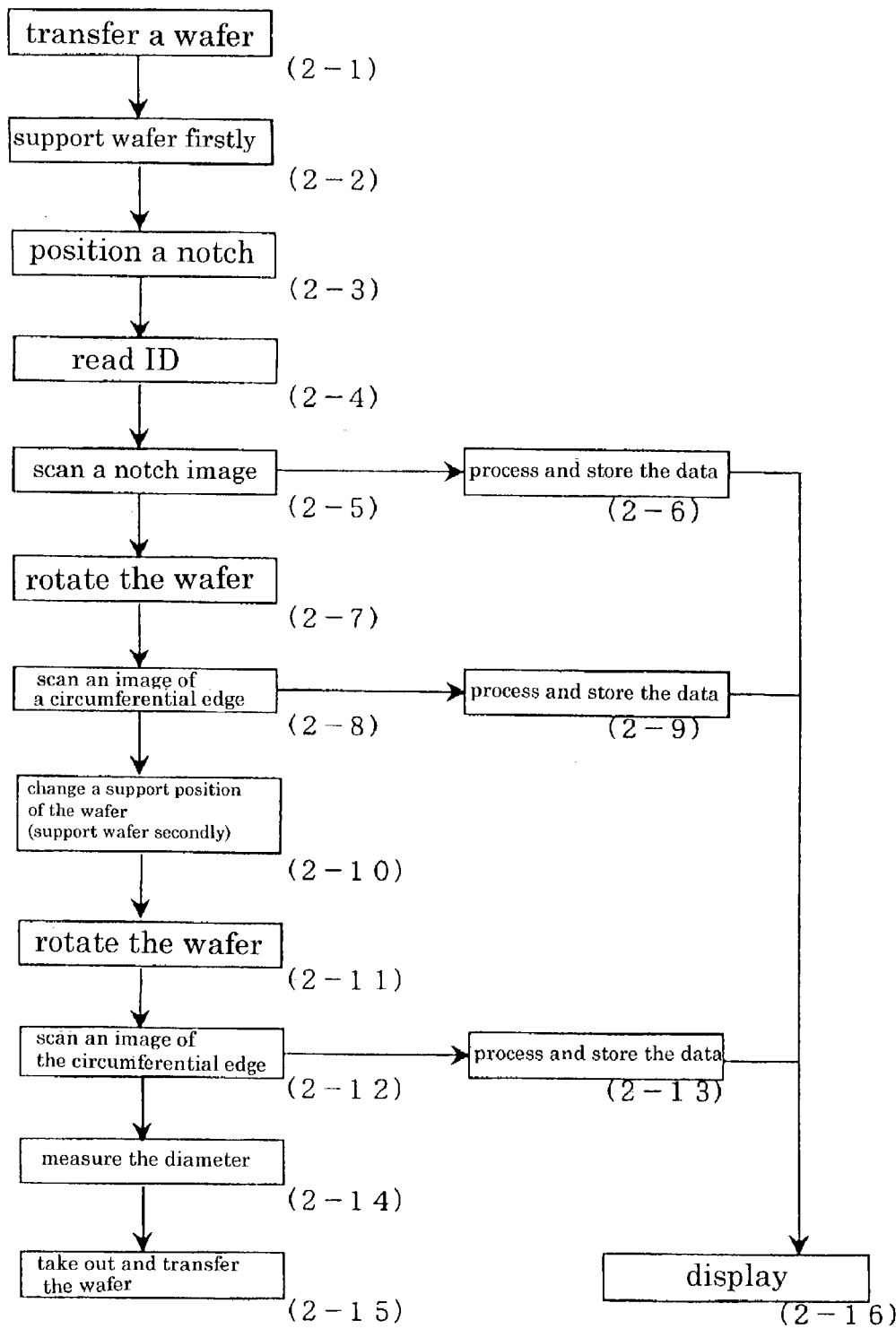
FIG. 31 is a flowchart showing a procedure of inspecting a wafer at a wafer inspection apparatus according to the present invention.

Each data is displayed (FIG. 31 (2-16)). By designating ID number of the wafer W, as shown in FIG. 18, the circumferential edge S of the wafer W can be displayed.

As shown in FIG. 18, on the screen displayed of the circumferential edge S of the wafer W, a first image data and a second image data can be optionally displayed. Here the circumferential edge displaying means 73 displays the circumferential edge S of the wafer W imaged by the plurality of imaging cameras 41 of the circumferential edge imaging means 40 in such a condition that each phase of the angle positions is matched. The images of the circumferential edge S of the wafer W can be scrolled along the peripheral direction of the circumferential edge S of the wafer W by the scroll means 74.

Particularly, the apex SS, the front side bevel SA, and the back side bevel SB of the circumferential edge S of the wafer W are aligned together for displaying. When operating the scroll bar 111, these three screens are moved together. Further, right-end, left-end, and center angle positions are displayed on an angle position display column 112.

The surface condition of the circumferential face, particularly the condition of the defect can be observed in view of the image screen of the circumferential edge S of the wafer W. In this case, the imaging camera for an apex 41 (SS), the imaging camera for a front side bevel 41 (SA), and the imaging camera for back side bevel 41 (SB) are positioned so that the imaging directions are at right angles to each face. Therefore, even if the circumferential edge S of the wafer W is beveled, whole part in the thickness direction can be imaged clearly. Accuracy for imaging is improved accordingly. Further, because the images can be scrolled, whole part can be observed clearly, which results improving accuracy.

While, as shown in FIG. 19, on the display screen of the notch N of the wafer W, the notch displaying means 75 simultaneously displays the images of the notch N of the wafer W imaged by the plurality of imaging cameras 51 of the notch imaging means 50. In detail, the apex SS, the front side bevel SA of the bottom Nt, the back side bevel SB of the bottom Nt, one side part Na, the side part SS, the other side part Nb, the side part SS, are displayed. In this case, because the image corresponding to each imaging camera 51 is obtained, relationship of relative positions of each image can be easily recognized.

Further, as shown in FIG. 2, FIG. 3, FIG. 4, and FIG. 5, when imaged by the bottom apex imaging camera 51 (SS(Nt)), the bottom front side bevel imaging camera 51 (SA(Nt)), the bottom back side bevel imaging camera 51 (SB(Nt)), one side part-apex imaging camera 51 (SS(Na)), and the other side part-apex imaging camera 51 (SS(Nb)), even if the upper and lower parts of the notch N is beveled, each face can be clearly observed. Accuracy is improved accordingly.

Each imaging camera 51 is positioned so as to be in the area of bright field of the reflected light by the illumination light from the notch illumination part 52. Therefore, the notch N can be clearly observed. Particularly, the defect can be imaged well. Each face can be clearly observed. Accuracy is improved accordingly.

Various kinds of data column are provided commonly on the screen of the circumferential edge S of the wafer W in FIG. 18 and the screen of the notch N of the wafer W.

The defect coordinate displaying means 81 displays the coordinate of the defect identified by the defect recognizing means 80 on the display 72. The defect coordinate displaying means 81 displays the angle coordinate along the peripheral direction for the circumferential edge S of the wafer W and displays the relative position along the thickness direction of the circumferential edge S of the wafer W. Because the position of the defect can be determined, the display becomes reliable and accuracy is improved accordingly.

The defect coordinate displaying means 81 sets the reference position of the notch for each screen and displays the defect position from the reference position. The reference position is set by the number of pixels from the right upper side of the screen. The defect coordinate is displayed by this reference position as the origin. Because the position of the defect can be determined, the display becomes reliable and accuracy is improved accordingly.

The defect form displaying means 83 displays the form identified by the defect form recognizing means 82 on the display 72. As shown in FIG. 18 and FIG. 19, these are displayed by classifying into one of point defects, line defects, and plane defects. Because the form of the defect can be categorized, accuracy is improved accordingly. Further, the defects are classified by the kinds, recognizing becomes easy.

The defect area displaying means 85 displays the area calculated by the defect area calculating means 84 on the display 72. Because the size of the defect can be categorized, accuracy is improved accordingly.

The defect circumscribed rectangle size displaying means 87 displays the size calculated by the defect circumscribed rectangle size calculating means 86 on the display 72. Specifically, the rough values of the length (the major axis) of the defect form and the width (the minor axis) are displayed. The size of the defect can be categorized. Accuracy is improved accordingly.

The defect density displaying means 90 displays the density of the defect calculated by the defect density calculating means 89. An extent of the defect can be categorized. Accuracy is improved accordingly.

The defect brightness displaying means 92 displays a mean brightness calculated by the defect brightness calculating means 91 on the display 72. Because the brightness of the defect corresponds to a depth of the defect, the depth of the defect can be recognized. Accuracy is improved accordingly.

The wafer quality displaying means 94 displays quality of the wafer W judged by the wafer quality judging means 93 on the display 72. If the judged results are good, "OK" is displayed. If the judged results are bad, "NO" is displayed. Because the quality of the wafer W can be automatically judged, inspection is easy.

A diameter displaying means 104 displays the diameter measured by the diameter measuring means 60 by corresponding the ID number. Further, if the diameter is in the rage of a common difference, it is recognized to be good, otherwise to be bad. Then it is displayed on the display 72.

Preferably, based on the results of the defect ranking means 100 and the defect distribution calculating means 101, for example, the table as shown in FIG. 27 and FIG. 28 is output by means of the display 72 or printers etc. Because the distribution state of the defects on the circumferential edge S or the extent of the defect can be recognized, it can be utilized for solution of defect generation. Accuracy of inspection is improved.

In the above embodiment, the wafer W with the notch N is an object to be inspected. This invention is not limited to the present embodiment. It can be applied for a wafer W with an orientation-flat. In this case, the notch imaging means 50 is changed appropriately for imaging the orientation-flat.

In the above embodiment, although the whole imaging cameras are used for imaging, this invention is not limited to this. Preferably, one, two or more imaging camera(s) can be used for imaging. It can be changed depending on the imaging condition.

In the above embodiment, although the circumferential edge S of the wafer W comprises three flat faces (namely the apex SS, the front side bevel SA, and the back side bevel SB), this invention can be applied to a wafer W with a circumferential edge S having other forms (e.g. a rounded form).

What is claimed is:

1. A wafer inspection apparatus comprising:
    a supporting means for rotatably supporting a wafer formed of a disk,
    a circumferential edge imaging means for imaging a circumferential edge of the wafer that is supported by the supporting means and rotated,
    a control means for processing image data imaged by the circumferential edge imaging means,
    wherein the circumferential edge imaging means includes a plurality of imaging cameras for imaging a plurality of different parts of the circumferential edge of the wafer, respectively,
    wherein the plurality of different parts include an apex, a front side bevel and a back side bevel, the apex being at right angles to a surface of the wafer, the front side bevel and the back side bevel being inclined relative to the apex,
    wherein the plurality of imaging cameras correspond to the apex, the front side bevel and the back side bevel, and wherein an apex imaging camera, a front side bevel imaging camera, and a back side bevel imaging camera are provided in such a condition that imaging directions thereof are at substantially right angles to the faces, respectively.

2. A wafer inspection apparatus according to claim 1, wherein a circumferential edge illumination part is provided for illuminating the circumferential edge of the wafer, and wherein the circumferential edge illumination part illuminates so that an illumination light focuses on a center of a certain arc formed along a thickness direction of the circumferential edge of the wafer, and wherein each imaging camera is positioned in a bright field of a reflection light by the illumination light from the circumferential edge illumination part positions.

3. A wafer inspection apparatus according to claim 1, wherein the control means is provided with an image data processing means and a display,
wherein the image data processing means displays images of the circumferential edge imaged by the apex imaging camera, the front side bevel imaging camera and the back side bevel imaging camera on the display in such a condition that each phase of the images is matched to an angle position of the wafer.

4. A wafer inspection apparatus according to claim 3, wherein the image data processing means is provided with
a defect recognizing means for recognizing an area with a certain difference of brightness compared to a standard brightness from the image data of the circumferential edge of the wafer.

5. A wafer inspection apparatus according to claim 4, comprising
an angle coordinate displaying function for displaying an angle coordinate along a peripheral direction of the circumferential edge of the wafer, and
a thickness direction coordinate displaying function for displaying a relative position along a thickness direction of the circumferential edge of the wafer.

6. A wafer inspection apparatus according to claim 3, comprising
a defect recognizing means for recognizing an area with a certain difference of brightness compared to a standard brightness from the image data of the circumferential edge of the wafer,
a defect form recognizing means for recognizing a form of the defect identified by the defect recognizing means, and
a defect form displaying means for displaying the form identified by the defect form recognizing means on the display.

7. A wafer inspection apparatus according to claim 6, wherein the defect form recognizing means has a function of classifying into each one of point defects, line defects, and plane defects and recognizing based on a predetermined threshold value.

8. A wafer inspection apparatus according to claim 7, having a defect distribution calculating means for calculating a distribution of the point defects, the line defects, and the plane defects at each certain angle unit for each image face of the imaging cameras.

9. A wafer inspection apparatus according to claim 3,
wherein a defect ranking means is provided for sizing in point defects, line defects, and plane defects at certain angles on the image face at each certain angle unit for each image face of the imaging cameras,
wherein the image data processing means is provided with
a defect area calculating means for calculating an area of the defect identified by the defect recognizing means,
a defect area displaying means for displaying the area calculated by the defect area calculating means on the display,
a defect circumscribed rectangle size calculating means for calculating a size of a circumscribed rectangle circumscribing the defect that is recognized by the defect recognizing means,
a defect circumscribed rectangle size displaying means for displaying the size calculated by the defect circumscribed rectangle size calculating means, and
wherein the image data processing means is provided with
a defect density calculating means for calculating a density of the defect from the area of the defect calculated by the defect area calculating means and the size of the circumscribed rectangle calculated by the defect circumscribed rectangle size calculating means,
a defect density displaying means for displaying the density of the defect calculated by the defect density displaying means on the display, and
wherein the image data processing means is provided with
a defect brightness calculating means for calculating a mean brightness of the defect identified by the defect recognizing means and
a defect brightness displaying means for displaying a mean brightness of the defect calculated by the defect brightness calculating means on the display, and
wherein the image data processing means is provided with
a quality judging means for judging quality of the wafer based on the defect obtained by the defect recognizing means and
a wafer quality displaying means for displaying quality of the wafer judged by the quality judging means.

10. A wafer inspection apparatus according to claim 1, wherein the wafer has a notch, and
wherein the circumferential edge imaging means is provided with
a bottom apex imaging camera that corresponds to an apex of a bottom of the notch,
a bottom front side bevel imaging camera that corresponds to a front side bevel of the bottom,
a bottom back side bevel imaging camera that corresponds to a back side bevel of the bottom,
one side part-apex imaging camera that corresponds to an apex of one side part of the notch, and
the other side part-apex imaging camera that corresponds to an apex of the other side part of the notch.

11. A wafer inspection apparatus according to claim 1, wherein the supporting means is provided with
a supporting board having a plurality of support fingers that are rotatably mounted around a central axis as a rotating center for supporting the circumferential edge of the wafer and provided on the circumference around the central axis, and
a driving means for rotating the supporting board, and
wherein each support finger is provided with a support face that is inclined downward to the central axis for supporting the circumferential edge of the wafer, and
wherein the supporting means is provided with a support position changing system for changing a support position of the wafer supported by the support fingers of the supporting board.

12. A wafer inspection apparatus according to claim 11, wherein the support position changing system is provided with a carrying board, and
wherein the carrying board is provided with a plurality of carrying fingers relatively rotatably provided around the same central axis with the supporting board for carrying the circumferential edge of the wafer on the circumference around the central axis, and
wherein the carrying board can move the carrying fingers to two positions, one position being a carrying position where the wafer is carried and lifted to a higher position than the support fingers of the supporting board, the other position being a delivery position where the wafer is delivered to the support fingers at a lower position than the support fingers, and wherein the support position changing system is provided with a moving system for moving two positions of the carrying position and the delivery position.

13. A wafer inspection apparatus according to claim 11, having a wafer transfer for transferring the wafer to be inspected from a storage of the wafer and centering the wafer to the support fingers of the supporting board and supporting.

14. A wafer inspection apparatus according to claim 13, wherein the wafer transfer means is provided with an engaging means for engaging the circumferential edge of the wafer, and wherein the wafer transfer means has a pair of carrying hands that can relatively move to two positions, one position being a carrying position where the engaging means is engaged to grasp the wafer in a face direction of the wafer and the other position being a carrying-release position where carrying is released, and wherein the engaging means has an elastic contact body for elastically contacting the wafer at the carrying position.

15. A wafer inspection apparatus according to claim 1, having a diameter measuring means for measuring a diameter of the wafer to be supported by the supporting means and rotated.

* * * * *